US007320881B2

(12) United States Patent
Lasker et al.

(10) Patent No.: US 7,320,881 B2
(45) Date of Patent: Jan. 22, 2008

(54) **RAPID IDENTIFICATION OF *NOCARDIA FARCINICA***

(75) Inventors: Brent A. Lasker, Atlanta, GA (US); June M. Brown, Decatur, GA (US)

(73) Assignee: The Government of the United States of America as Represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 11/100,338

(22) Filed: Apr. 6, 2005

(65) Prior Publication Data

US 2005/0277136 A1 Dec. 15, 2005

Related U.S. Application Data

(60) Provisional application No. 60/560,867, filed on Apr. 9, 2004.

(51) Int. Cl.
*C12P 19/34* (2006.01)
*C07H 21/04* (2006.01)

(52) U.S. Cl. .................................... 435/91.2; 536/24.3

(58) Field of Classification Search .................... None
See application file for complete search history.

(56) References Cited

U.S. PATENT DOCUMENTS 4,683,195 A * 7/1987 Mullis et al. .................. 435/6
5,645,994 A 7/1997 Huang

OTHER PUBLICATIONS

Genbank, ACCESSION BG854275, 2001, National Center for Biotechnology Information, 8600 Rockville Pike, Bethesda, MD 20894. Also found at: http://www.ncbi.nlm.nih.gov/entrez/viewer.fcgi?db=nucleotide&val=14235459.*

Genbank, ACCESSION AF078669, 1998, National Center for Biotechnology Information, 8600 Rockville Pike, Bethesda, MD 20894. Also found at: http://www.ncbi.nlm.nih.gov/entrez/viewer.fcgi?db=nucleotide&val=3834558.*

Buck et al., Design Strategies and Performance of Custom DNA Sequencing Primers, Sep. 1999, Bio Techniques 27: 528-536.*

Coyne et al., PCR Primer Design and Reaction Optimisation, Molecular Biology Techniques Manual Third Edition, copyright 2001, retrieved from thw world wide web on Mar. 6, 2007 at: http://www.mcb.uct.ac.za/pcroptim.htm.*

Berd, D. "Laboratory identification of clinically important aerobic actinomycetes" *Appl. Microbiol.* 25:665-681 (1973).

Biehle et al. "Novel method for rapid identification of *Nocardia* species by detection of preformed enzymes" *J. Clin. Microbiol.* 34:103-107 (1996).

Blumel et al. "Typing of *Nocardia farcinica* by pulsed-field gel electrophoresis reveals an endemic strain as source of hospital infections" *J. Clin. Microbiol.* 36:118-122 (1998).

Boiron et al. "*Nocardia*, nocardoisis and mycetoma" *Med. Mycol.* 36 Suppl 1:26-37 (1998).

Brown et al. "Rapid Identification of *Nocardia farcinica* clinical isolates by a PCR assay targeting a 314-Base-Pair Species-specific DNA Fragment" *J Clinical Microbiol* 42(8):3655-60 (2004).

Cohen et al. "Unilateral vocal cord paralysis as a result of a *Nocardia farcinica* laryngeal abscess" *Eur. J. Clin. Microbiol. Infect. Dis.* 19:224-227 (2000).

Conville et al. "*Nocardia veterana* as a pathogen in North American patients" *J. Clin. Microbiol.* 41:2560-2568 (2003).

Conville et al. "Identification of *Nocardia* species by restriction endonuclease analysis of an amplified portion of the 16S rRNA gene" *J. Clin. Microbiol.* 38:158-164 (2000).

Desmond et al. "Mouse pathogenicity studies of *Nocardia asteroides* complex species and clinical correlations with human isolates" *FEMS Microbiol. Lett.* 110:281-284 (1993).

Ellsworth et al. "Artifactual variation in randomly amplified polymorphic DNA banding patterns" *BioTechniques* 14:214-217 (1993).

Exmelin et al. "Molecular study of nosocomial nocardiosis outbreak involving heart transplant recipients" *J. Clin. Microbiol.* 34:1014-1016 (1996).

Gibbons et al. "PCR-ELISA: a new simplified tool for tracing the source of cryptosporidiosis in HIV-positive patients" *Parasitol Res* 87:1031-4 (2001).

Guillot et al. "PCR-DNA probe assays for identification and detection of *Prevotella intermedia* sensu stricto and *Prevotella nigrescens*" *J. Clin. Microbiol.* 35: 1876-1882 (1997).

Gutierrez et al. "A quantitative PCR-ELISA for the rapid enumeration of bacteria in refrigerated raw milk" *J. Appl. Microbiol.* 83(4):518-23 (1997).

(Continued)

*Primary Examiner*—Kenneth R. Horlick
*Assistant Examiner*—Mark Staples
(74) *Attorney, Agent, or Firm*—Klarquist Sparkman, LLP

(57) ABSTRACT

Provided are *Nocardia farcinica*-specific primers comprising the nucleotide sequence of SEQ ID NO:1-39. Provided is a polynucleotide represented by SEQ ID NO:41 and SEQ ID NO:40. Further provided is a method of identifying a *Nocardia farcinica* infection in a subject with the primer identified by SEQ ID NO:1-39, or detecting the presence of a polynucleotide consisting of the nucleotide sequence represented by SEQ ID NO:40 or SEQ ID NO:41. Also provided is a method of identifying *Nocardia farcinica* infection in a subject by amplifying DNA from the subject using a *Nocardia farcinica*-specific primer comprising a nucleotide sequence selected from the group consisting of SEQ ID NO:1-39. Further provided is a kit for identifying *Nocardia farcinica* comprising a *Nocardia farcinica*-specific primer comprising SEQ ID: NO:1-39 and a kit for identifying *Nocardia farcinica* comprising a *Nocardia farcinica* specific primer capable of amplifying SEQ ID NO:41.

3 Claims, 4 Drawing Sheets

OTHER PUBLICATIONS

Figure 1:
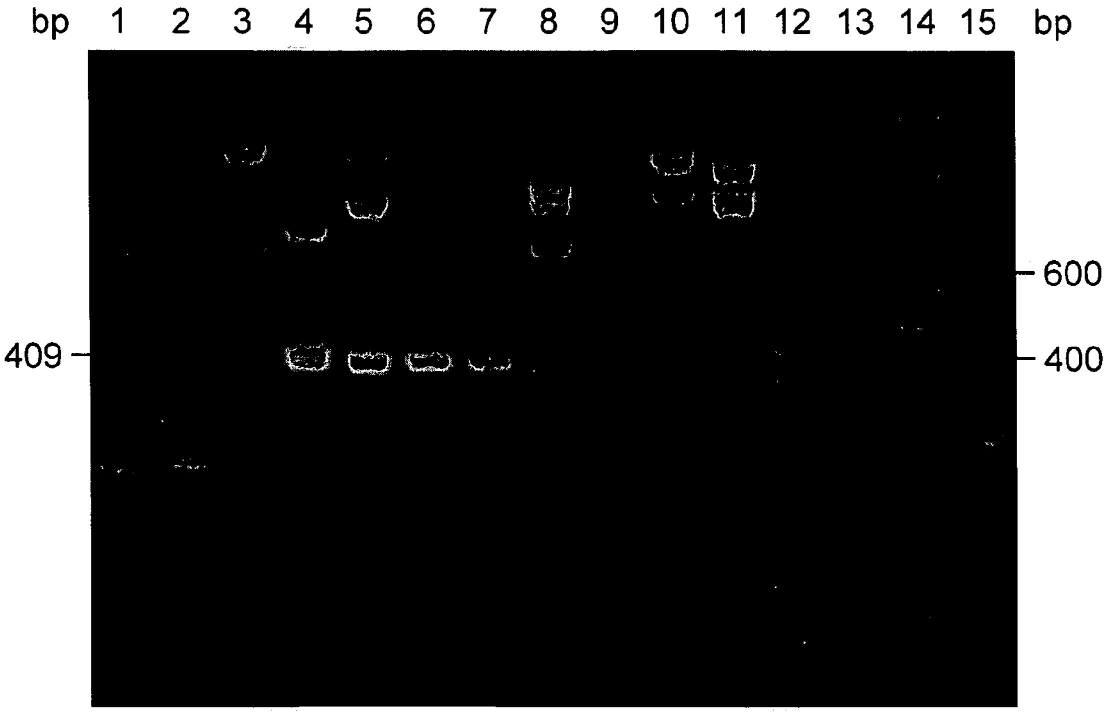

Heintges et al. "Quantitative hepatitis C RNA-polymerase chain reaction and detection with DNA-ELISA" *Hepatogastroenterology* 45:1684-9 (1998).

Isik et al. "Differentiation of *Nocardia* species by PCR-randomly amplified polymorphic DNA fingerprinting" *Syst. Appl. Microbiol.* 25:60-67 (2002).

Kiska et al. "Identification of medically relevant *Nocardia* species with an abbreviated battery of tests" *J. Clin. Microbiol.* 40:1346-1351 (2002).

Laurent et al. "Rapid identification of clinically relevant *Nocardia* species to genus level by 16S rRNA gene PCR" *J. Clin. Microbiol.* 37:99-102 (1999).

Laurent et al. "Genetic relatedness analysis of Nocardia strains by random amplification polymorphic DNA: validation and applications" *Research in Microbiology* 151(4):263-70 (2000).

Lentnek et al. "Use of arbitrarily primed PCR (AP-PCR) for the differentiation of *Nocardia farcinica* from other members of the *Nocardia asteroides* complex" *Abstracts of the 97th Interscience Conference on Antimicrobial Agents* Abstract D-75:96 (1997).

Loffler et al. "Detection of PCR-amplified fungal DNA by using a PCR-ELISA system" *Med Mycol* 36(5):275-9 (1998).

Lungu et al. "Differntiation of *Nocardia* from rapidly growing *Mycobacterium* species by PCR-RFLP analysis" *Diagn. Microbiol. Infect. Dis.* 18: 13-18 (1994).

Manninen et al. "Highly presumptive identification of bacterial isolates associated with the recent Canada-wide *Mastitis epizootic* as *Nocardia farcinica*"*Can. J. Microbiol.* 39:635-641 (1993).

Manulis et al. "Sensitive and specific detection of *Xanthomonas campestris* pv. *pelargonii* with DNA primers and probes identified by random amplified polymorphic DNA analysis" *Appl. Environ. Microbiol.* 60: 4094-4099 (1994).

Martin-Sanchez et al. "Diagnosis of infections with *Leishmania infantum* using PCR-ELISA" *Parasitology* 122(Pt. 6):607-15 (2001).

McNeil et al. "The medically important aerobic actinomycetes: epidemiology and microbiology" *Clin. Microbiol. Rev.* 7:357-417 (1994).

McNeil et al. *Nocardia*, p.481-500. *In* V. L. Yu, R. Weber, and D. Raoult (ed.), "Antimicrobial therapy and vaccines" Apple Trees Productions, LLC, New York (2002).

Muir et al. "Use of the BioMerieux ID 32C yeast identification system for identification of aerobic actinomycetes of medical importance" *J. Clin. Microbiol.* 35:3240-3233 (1997).

Palittapongarnpim et al. "DNA fragment length polymorphism analysis of *Mycobacterium tuberculosis* isolates by arbitrarily primed PCR" *J Infect Dis* 167:975-78 (1993).

Pham et al. "Rapid Identification of *Nocardia farcinica* clinical isolates by a PCR assay targeting a 314-Base-Pair Species-specific DNA Fragment" *Power Point Poster presentation at Emory University*. (Apr. 24, 2000).

Pinero et al. "PCR-ELISA for diagnosis of *Mucocutaneous leishmaniasis*" *Acta Trop* 73(1):21-9 (1999).

Rola et al. "The detection of bovine leukemia virus proviral DNA by PCR-ELISA" *J Virol Methods* 99(1-2):33-40 (2002).

Roth et al. "Phylogeny of the Genus *Nocardia* based on reassessed 16S rRNA gene sequences reveals underspeciation and division of strains classified as *Nocardia asteroides* into three established species and two unnamed taxons" *J. Clin. Microbiol.* 41:851-856 (2003).

Sails et al. "Development of a PCR ELISA assay for the identification of *Campylobacter jejuni* and *Campylobacter coli*" *Mol Cell Probes* 15(5):291-300 (2001).

Schaal et al. "Actinomycete infections in humans-a review" *Gene* 15:201-211 (1992).

Scheu et al. "Rapid detection of *Listeria monocytogenes* by PCR-ELISA" *Lett Appl Microbiol* 29(6):416-20 (1999).

Seal et al. "Isolation of a *Pseudomonas solanacearum*-specific DNA probe by subtraction hybridization and construction of species-specific oligonucleotide primers for sensitive detection by the polymerase chain reaction" *Appl. Environ. Microbiol.* 58:3751-3758 (1992).

Shamloul et al. "Sensitive detection of the Egyptian species of sugarcane streak virus by PCR-probe capture hybridization (PCR-ELISA) and its complete nucleotide sequence" *J. Virol Methods* 92(1):45-54 (2001).

Stackebrandt et al. "Taxonomic note: a place for DNA-DNA reassociation and 16S rRNA sequence analysis in the present species definition in bacteriology" *Int J Syst Bacteriol* 44:846-849 (1994).

Steingrube et al. "DNA amplification and restriction endonuclease analysis for differentiation of 12 species and taxa of *Nocardia*, including recognition of four new taxa within the *Nocardia asteroides* complex" *J. Clin. Microbiol.* 33:3096-3101 (1995).

Steingrube et al. "Rapid identification of clinically significant species and taxa of *Aerobic actinomycetes*, including *Actinomadura, Gordona, Nocardia, Rhodococcus, Streptomyces*, and *Tsukamurella* isolates, by DNA amplification and restriction endonuclease analysis" *J Clinical Microbiol* 35:817-822 (1997).

Tapchaisri et al. "Detection of *Salmonella* contamination in food samples by dot-ELISA, DNA amplification and bacterial culture" *Asian Pac J Allergy Immunol* 17:41-51 (1999).

Teng et al. "PCR assay for species-specific identification *of Bacteroides thetaiotaomicron.*" *J. Clin. Microbiol.* 38:1672-1675 (2000).

Torres et al. "Infection caused by *Nocardia farcinica*: case report and review" *Eur. J. Clin. Microbiol. Infect. Dis.* 19:205-212 (2000).

Venturoli et al. "Detection of adeno-associated virus DNA in female genital samples by PCR-ELISA" *J Med Virol* 64:577-82 (2001).

Wallace et al. "Antimicrobial susceptibility patterns of *Nocardia asteroides.*" *Antimicrob. Agents Chemother.* 32:1776-1779 (1988).

Wallace et al. "Cefotaxime-resistant *Nocardia asteroides* strains are isolates of the controversial species *Nocardia farcinica.*" *J. Clin. Microbiol.* 28:2726-2732 (1990).

Wenger et al.. "*Nocardia farcinica* sternotomy site infections in patients following open heart surgery." *J. Infect. Dis.* 178:1539-1543 (1998).

Wilson et al. "Clinical application of PCR-restriction enzyme pattern analysis for rapid identification of *Aerobic actinomycete* isolates" *J. Clin. Microbiol.* 36:148-152 (1998).

Yassin et al. "*Nocardia puris* sp. nov." *Int. J. Syst. Evol. Microbiol.* 53:1595-1599 (2003).

* cited by examiner

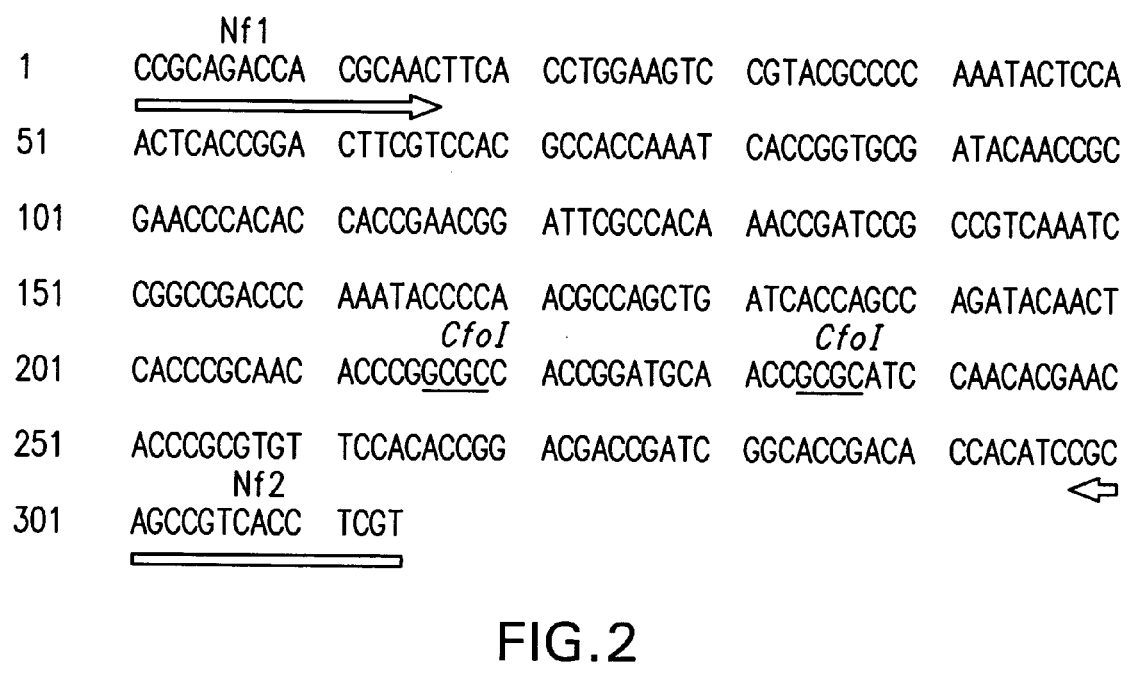

Nf1

1 CCGCAGACCA CGCAACTTCA CCTGGAAGTC CGTACGCCCC AAATACTCCA

51 ACTCACCGGA CTTCGTCCAC GCCACCAAAT CACCGGTGCG ATACAACCGC

101 GAACCCACAC CACCGAACGG ATTCGCCACA AACCGATCCG CCGTCAAATC

151 CGGCCGACCC AAATACCCCA ACGCCAGCTG ATCACCAGCC AGATACAACT

*CfoI* *CfoI*

201 CACCCGCAAC ACCCGGCGCC ACCGGATGCA ACCGCGCATC CAACACGAAC

251 ACCCGCGTGT TCCACACCGG ACGACCGATC GGCACCGACA CCACATCCGC

Nf2

301 AGCCGTCACC TCGT

FIG. 2

RAPID IDENTIFICATION OF *NOCARDIA FARCINICA*

CROSS-REFERENCE TO RELATED APPLICATIONS

This application claims the benefit of U.S. Provisional Application No. 60/560,867, filed on Apr. 9, 2004. The aforementioned application is herein incorporated by reference in its entirety.

BACKGROUND

Members of the genus *Nocardia*, which are partially acid-fast, aerobic, branched gram-positive bacilli, are opportunistic pathogens commonly found in patients with acute or chronic, suppurative or granulomatous diseases (McNeil and Brown (1994) Clin. Microbiol. Rev. 7: 357-417). Of the greatest clinical importance within this genus is *Nocardia farcinica*, a member of the *N. asteroides* complex composed of *Nocardia abscessus, Nocardia asteroides* sensu stricto type VI (*Nocardia cyriacigeorgica*), *Nocardia nova*, and *Nocardia farcinica* (Wallace et al., (1988) Antimicrob. Agents Chemother. 32:1776-1779). *Nocardia farcinica* causes localized and disseminated infections, predominantly affecting immunocompromised patients. Differentiation of *Nocardia farcinica* from other members of *N. asteroides* complex is important because *Nocardia farcinica* has a high degree of resistance to various antibiotics, especially to the third-generation cephalosporins, which may make it difficult to treat (Wallace et al., (1988) Antimicrob. Agents Chemother. 32:1776-1779; Wallace et al., (1990) J. Clin. Microbiol 28:2726-2732) and because mouse pathogenicity studies have demonstrated that it may be more virulent than the other *N. asteroides* complex species (Desmond and Flores (1993) FEMS Microbiol. Lett. 110: 281-284).

Human and animal clinical infections with *Nocardia farcinica* may occur more frequently than previously recognized (Cohen et al., (2000) Eur. J. Clin. Microbiol. Infect. Dis. 19: 224-227; Manninen et al., (1993) Can. J. Microbiol. 39: 635-641; Torres et al., Eur. J. Clin. Microbiol Infect. Dis. 19: 205-212). Other reports from France, Germany, and the United States have implicated *Nocardia farcinica* as the cause of postoperative wound infections in patients undergoing cardiac and other vascular surgeries (Blumel et al., (1998) J. Clin. Microbiol. 36:118-122; Boiron et al., (1998) Med. Mycol. 36 Suppl 1: 26-37; Exmelin et al., J. Clin. Microbiol. 34: 1014-1016; Wenger et al., (1998) J. Infect. Dis. 178: 1539-1543). From 1987 through 1989, one of the largest known nocardial mastitis epizootics was reported in all 10 Canadian provinces (Manninen et al., (1993) Can. J. Microbiol. 39: 635-641). The causative agent of the outbreak was initially reported as *Nocardia* species, but later was presumptively identified as *Nocardia farcinica* (Manninen et al., (1993) Can. J. Microbiol. 39: 635-641). Further phenotypic and molecular testing at the Actinomycete Reference Laboratory confirmed the identification. It is important to rapidly identify the pathogen not only for antimicrobial therapeutic purposes, but also to establish the spectra of disease and to monitor and control the rate of infection.

Traditional biochemical identification of *Nocardia farcinica* is often laborious, difficult to replicate, and time-consuming; species identification usually requires up to 3 weeks. In addition, misidentification of *Nocardia farcinica* may occur because of the phenotypic similarity to species in the related genera, *Gordonia, Rhodococcus*, and rapidly growing *Mycobacterium*. Commercially available systems in combination with a few traditional tests have shortened the identification time of *Nocardia* species to 7 days; however, phenotypic identification to the species level within this genus remains problematic (Biehle et al. (1996) J. Clin. Microbiol. 34: 103-107; Kiska et al., (2002) J. Clin. Microbiol. 40:1346-1351; Muir and Pritchard (1997) J. Clin. Microbiol. 35: 3240-3233). For example, within the genus *Nocardia* are recently described species, *Nocardia africana, Nocardia vaccinii*, and *Nocardia veterana*, that share similar phenotypic (biochemical and susceptibility profiles) and molecular characteristics to *N. nova* (Conville et al., (2003) J. Clin. Microbiol. 41: 2560-2568). The use of molecular approaches such as PCR targeting portions of the hsp gene and the 16S rRNA gene coupled with restriction endonuclease digestion of PCR products has been the focus of recent investigations for the separation of mycobacteria from the nocardiae as well as for the recognition of species within the genera *Mycobacterium* and *Nocardia* (Conville et al., (2003) J. Clin. Microbiol. 41: 2560-2568; Conville et al., (2000) J. Clin. Microbiol. 38: 158-164; Laurent et al., (1999) J. Clin. Microbiol. 37: 99-102); Lungu et al., (1994) Diagn. Microbiol. Infect. Dis. 18: 13-18; Steingrube et al., (1995) J. Clin. Microbiol. 33: 3096-3101; Wilson et al., (1998) J. Clin. Microbiol. 36:148-152). Such methodology has proven to be sensitive, less time-consuming, and less labor-intensive than traditional biochemical methods. However, accurate identification may still be difficult because it relies upon analysis of a relatively few restriction fragments from a single gene, many of which co-migrate between different species. Recently, randomly amplified polymorphic DNA (RAPD) analysis has been described as an identification method for the *Nocardia* species (Isik and Goodfellow (2002) Syst. Appl. Microbiol. 25:60-67). RAPD analysis has also been described as a useful method for intraspecies discrimination in an epidemiological study of *Nocardia farcinica* (Exmelin et al., J. Clin. Microbiol. 34: 1014-1016). Exmelin et al. (Exmelin et al., J. Clin. Microbiol. 34: 1014-1016), using RAPD analysis for subtyping, incorporated a single short primer, DKU49, in a low stringency PCR to amplify genomic DNA. While relatively easy to perform, identification based on RAPD profiles suffers from the disadvantage of lacking reproducible profiles unless stringent reaction conditions are observed. For instance, profiles were determined to be dependent on reaction parameters such as annealing temperature, magnesium concentration, the type of thermal cycler, source of DNA polymerase, and both primer and template concentrations. In addition, except for a pronounced 409-bp band, variation of DKU49 profiles were observed among strains of *Nocardia farcinica* making identification based on RAPD profiles alone difficult (FIG. 1). No correlation between RAPD profiles and epidemiologic relatedness was observed.

To overcome the above disadvantages, compositions and methods to identify *Nocardia farcinica* are disclosed.

SUMMARY OF THE INVENTION

Provided herein are compositions and methods designed to identify *Nocardia farcinica*. Provided herein are *Nocardia farcinica*-specific primers. Further provided is a method of identifying a *Nocardia farcinica* infection in a subject, comprising contacting DNA from the subject with a *Nocardia farcinica*-specific primer. Further provided is a method of identifying a *Nocardia farcinica* infection in a subject, comprising detecting the presence of a *Nocardia farcinica*- specific polynucleotide. Further provided is a kit for identifying *Nocardia farcinica* comprising a *Nocardia farcinica*-specific primer.

BREIF DESCRIPTION OF THE DRAWINGS

The accompanying drawings, which are incorporated in and constitute a part of this specification, illustrate several aspects described below.

FIG. 1 shows randomly amplified polymorphic DNA patterns of *Nocardia farcinica* and related species. Lanes 1-3, *N. nova* isolates, W6310, W6311, and ATCC 33726$^T$, lanes 4-7, *Nocardia farcinica* isolates, ATCC 3318$^T$, W6434, W6017, and W6255; lane 8, *N. brasiliensis*, ATCC 19296$^T$; lane 9, *Mycobacterium fortuitum*, ATCC 6841 T; lane 10, *N. transvalensis*, ATCC 6865$^T$; lane 11, *N. brasiliensis*, W6312; lane 12, *N. asteroides*, ATCC 19247$^T$; lanes 13 and 14, *N. abscessus*, W6133 and W6335; and lane 15, *N. asteroides* sensu stricto type VI isolate, W6344. The molecular size standard consisting of a 100-bp DNA ladder is shown on the right margin. The 409-bp fragment for four strains of *Nocardia farcinica* (lanes 4 to 7) is shown on the left margin.

FIG. 2 shows the DNA sequence of the 314-bp fragment (SEQ ID NO:41) obtained for *Nocardia farcinica* isolates ATCC 3318$^T$, W6021, W6032, W6954, and W6889. The PCR primers Nf1 (SEQ ID NO:1) and Nf2 (SEQ ID NO:2) are designated by arrows. The two CfoI sites are underlined.

Figure 3:
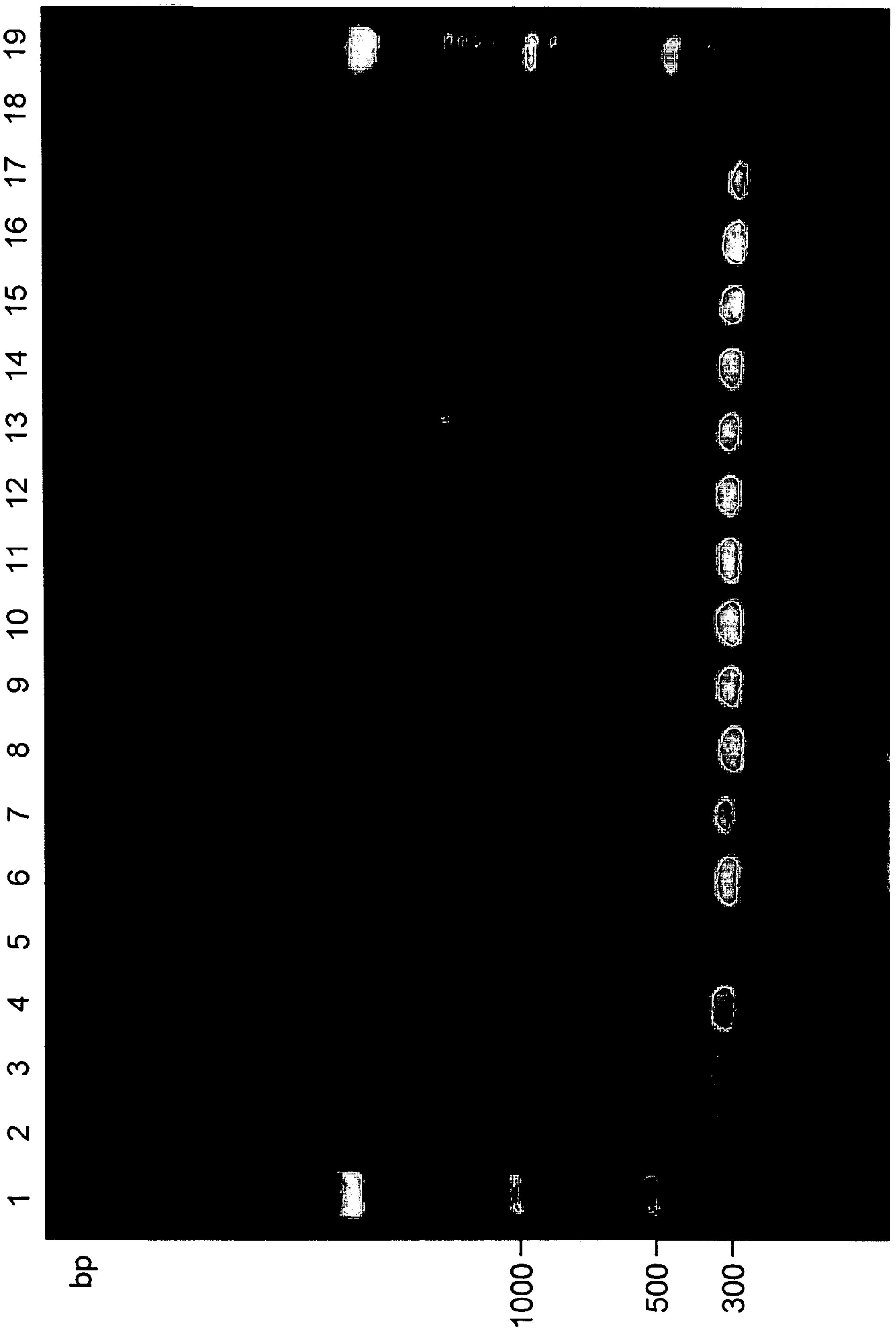

FIG. 3 shows specific amplification of the 314-bp DNA fragment for 17 strains of *Nocardia farcinica* using primers Nf1 and Nf2. Lanes 1 and 19, the molecular size standard consisting of a 100-bp DNA ladder; lanes 2-17, *Nocardia* farcinica, ATCC 3318$^T$, W5185, W5492, W5555, W5871, W5952, W6500, W6544, W6859, W6866, W6889, W6925, W6954, W6993, W7022, and W7028; and lane 18, negative control containing no template DNA.

Figure 4:
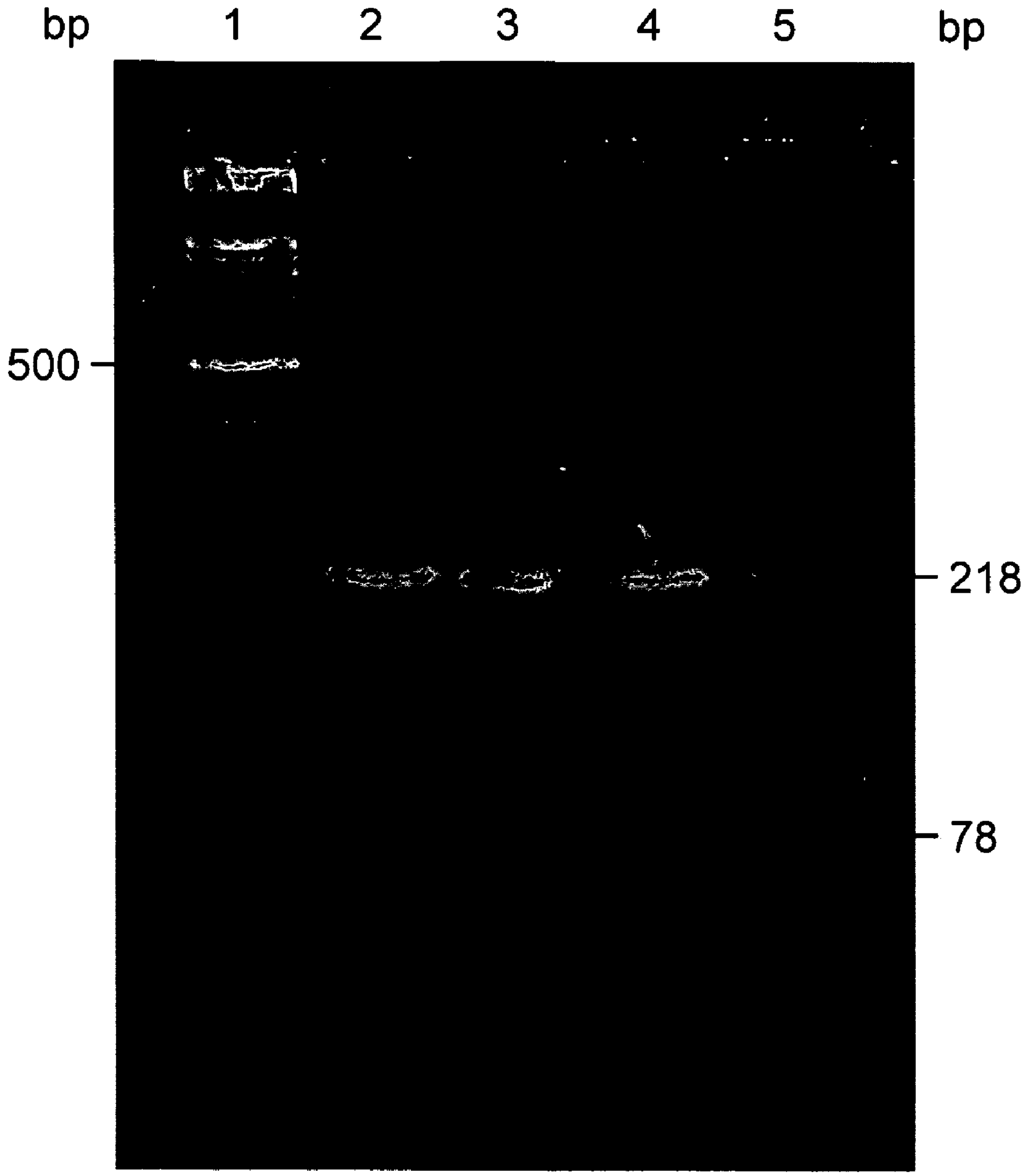

FIG. 4 shows restriction endonuclease digestion of the 314-bp fragment using CfoI from four strains of *Nocardia farcinica*. Lane 1, the molecular size standard consisting of a 100-bp DNA ladder; lanes 2-5, *Nocardia farcinica* W6032, W6021, W6954, and W6889. The 218-bp and 78-bp CfoI restriction fragments are shown on the right margin.

DETAILED DESCRIPTION

Provided herein are methods and compositions for identifying *Nocardia farcinica.*

As used in the specification and the appended claims, the singular forms “a,” “an” and “the” include plural referents unless the context clearly dictates otherwise. Thus, for example, reference to “a pharmaceutical carrier” includes mixtures of two or more such carriers, and the like.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

Provided herein is a *Nocardia farcinica*-specific primer. For example, the disclosed primers are capable of hybridizing with the disclosed nucleic acids, such as the SEQ ID NO:40 or SEQ ID NO:41, or with a *Nocardia farcinica*-specific nucleic acid, such as a *Nocardia farcinica*-specific fragment of SEQ ID NO:40 or 41. A *Nocardia farcinica*-specific primer comprising the nucleotide sequence of SEQ ID NO:1 and further provided is a *Nocardia farcinica*-specific primer comprising the nucleotide sequence of SEQ ID NO:2. Also provided are *Nocardia farcinica*-specific primers comprising a nucleotide sequence selected from the group consisting of SEQ ID NOS:3-39. The nucleic acids in SEQ ID NOS:1-39 constitute a representative set of primers defined by SEQ ID NO:40.

In one aspect, the primer or fragment can exclude any one or more of the polynucleotides of SEQ ID NOS:1-48 and 52-54. In one aspect the primer is not a primer selected from the group consisting of SEQ ID NOS:22-26, 52, 53 and 54.

In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids.

The term hybridization typically means a sequence driven interaction between at least two nucleic acid molecules, such as a primer or a probe and a gene. A sequence driven interaction is an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions.

For example, when the nucleic acids are used as probes stringency of hybridization can be controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art. In one aspect, probes include, but are not limited to SEQ ID NO:40 and SEQ ID NO:41. Also disclosed are any sub region of SEQ ID NOS:40 and 41 that are large enough to function as a probe.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is present, for example, at 10- or 100- or 1000-fold excess. This type of assay can be performed under conditions where both the limiting and non-limiting primer are for example, 10-fold or 100-fold or 1000-fold below their $k_d$, or where only one of the nucleic acid molecules is 10-fold or 100-fold or 1000-fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would exist when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

It is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

As used herein, it is understood that *Nocardia farcinica*-specific means that a primer, probe, sequence, polypeptide, nucleic acid (polynucleotide) or other disclosed molecule is species-specific for *Nocardia farcinica*. Species-specific means that the polynucleotide or polypeptide is not found identically in any other species. For example, comparison with known or newly identified sequences can be performed using BLAST algorithm software. The BLAST algorithm can perform a statistical analysis of the similarity between two sequences (see, for example, Karlin and Altschul, Proc. Natl. Acad. Sci. USA 90:5873, 1993, which is incorporated herein by reference). In one aspect, a *Nocardia farcinica*-specific primer is a primer that allows for selective amplification of *Nocardia farcinica* species-specific polynucleotide under stringent PCR conditions, but does not amplify polynucleotides of other *Nocardia* species or of any other species. Such *Nocardia farcinica* species-specific polynucleotides include, but are not limited to, SEQ ID NOS:1-47. Non-limiting examples of *Nocardia* farcinica-specific primers include SEQ ID NOS:1-39.

Provided herein is a polynucleotide consisting of the nucleotide sequence represented by SEQ ID NO:41. This is a 314 base pair nucleotide fragment that is *Nocardia farcinica*-specific. Also provided herein is a polynucleotide consisting of the nucleotide sequence represented by SEQ ID NO:40. This is a 409 base pair nucleotide fragment that is *Nocardia farcinica*-specific.

A polynucleotide comprising naturally occurring nucleotides linked by phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., Biochemistry 34:11363-11372 (1995)).

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

Fragments of disclosed nucleotides are provided herein. A fragment of a reference nucleic acid contains only contiguous nucleotides of the reference nucleic acid and is at least one nucleotide shorter than the reference sequence. Similarly, a fragment of a reference protein or polypeptide includes only contiguous amino acids of the reference protein/polypeptide, and is at least one amino acid shorter than the reference sequence. A *Nocardia farcinica*-specific fragment of a nucleic acid or protein has a nucleotide or amino acid sequence found only in *Nocardia farcinica*. The term "fragment" or "restriction fragment" also is used herein to refer to a product that can be produced by an enzymatic reaction on a polynucleotide sequence, i.e., a nucleotide produced upon cleavage of a phosphodiester bond in the polynucleotide. Although the term "restriction fragment" is used generally herein to refer to a nucleotide that can be produced by a restriction enzyme reaction, it should be recognized that the fragment need not necessarily be produced by a restriction enzyme reaction, but also can be produced using methods of chemical synthesis to produce a synthetic nucleotide that is equivalent to a restriction fragment. It should be recognized that the terms "polynucleotide", "nucleotide" or "fragment" are not used herein to suggest a particular size or number of nucleotides comprising the molecule, and that a nucleotide or fragment of the invention can contain up to several nucleic acids or more.

Provided herein is a *Nocardia farcinica*-specific fragment of the nucleic acid SEQ ID NO:41. Also provided is a *Nocardia farcinica* specific fragment of SEQ ID NO:41, wherein the fragment is a restriction fragment. In one aspect, the restriction fragment of SEQ ID NO:41 is made using Cfo I. Such a Cfo I restriction fragment may be selected from the group consisting of SEQ ID NOS:42-44. Another fragment provided herein is a *Nocardia farcinica*-specific fragment of the nucleic acid SEQ ID NO:40. Also provided herein is a *Nocardia farcinica*-specific fragment of SEQ ID NO:40, wherein the fragment is a restriction fragment. In one aspect, the restriction fragment of SEQ ID NO:40 is made using Cfo I. Such a Cfo I fragment may be selected from the group consisting of SEQ ID NO:43, 45-47. It would be clear to those skilled in the art that other restriction enzymes could be used to produce *Nocardia farcinica*-specific fragments of the disclosed nucleotide sequences. The provision for fragments and restriction fragments of the disclosed nucleotides is intended to encompass fragments made by other restriction enzymes which may be of varying lengths and nucleotide sequence.

Provided are peptides or polypeptides encoded by the disclosed nucleotide sequences. Provided are any of the peptides produced by the process of expressing any of the disclosed nucleic acids. Polypeptides can be encoded by the disclosed nucleotide sequences. For example, encoded polypeptides include SEQ ID NOS:49-51. The disclosed nucleotide sequences comprise at least three open reading frames, two of which have stop codons. Polypeptides encoded by each open reading frame are disclosed. An isolated *Nocardia farcinica*-specific polypeptide encoded by a *Nocardia farcinica*-specific nucleic acid is provided. The isolated polypeptide can be encoded by a nucleic acid selected from the group consisting of SEQ ID NOS:1-48, 52, 53 and 54.

In one aspect, the isolated polypeptide can exclude any one or more of the polypeptides encoded by SEQ ID NOS:1-48 and 52-54. Also provided are the isolated peptides, wherein the peptide does not include SEQ ID NOS: 49-51. In one aspect, the isolated peptide is not encoded by SEQ ID NOS: 52-54.

Peptides or polypeptides encoded by the disclosed nucleotide sequences can be used for vaccines or to detect antibodies from a subject directed to the peptides or polypeptides.

The peptides or polypeptides of can be used in the construction of a vaccine comprising an immunogenic amount of the peptide or polypeptide and a pharmaceutically acceptable carrier. The vaccine can be a peptide of the present embodiments or a peptide bound to a carrier or a mixture of bound or unbound antigens. The vaccine can then be used in a method of preventing *Nocardia farcinica* infection in a subject. The term subject as used throughout the specification includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

Immunogenic amounts of the peptide can be determined using standard procedures. Briefly, various concentrations of a putative specific immunoreactive peptides or polypeptides are prepared, administered to an animal and the immunological response (e.g., the production of antibodies or cell-mediated response) of an animal to each concentration is determined.

The pharmaceutically acceptable carrier in the vaccine can comprise saline or other suitable carriers (Arnon, R. (Ed.) Synthetic Vaccines I:83-92, CRC Press, Inc., Boca Raton, Fla., 1987). By "pharmaceutically acceptable" is meant a material that is not biologically or otherwise undesirable, i.e., the material may be administered to a subject, along with the peptide, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The vaccine may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the vaccine by inhalant can be through the nose or mouth via delivery by a spraying or droplet mechanism. Delivery can also be directly to any area of the respiratory system (e.g., lungs) via intubation. The exact amount of the vaccine required will vary from subject to subject, depending on the species, age, weight and general condition of the subject, the severity of the disorder being treated, the particular peptide, its mode of administration and the like. Thus, it is not possible to specify an exact amount for every peptide that may be included in the vaccine. However, an appropriate amount can be determined by one of ordinary skill in the art using only routine experimentation given the teachings herein.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. These most typically would be standard carriers for administration of drugs to humans or animals, including solutions such as sterile water, saline, and buffered solutions at physiological pH.

A vaccine may include carriers, thickeners, diluents, buffers, preservatives, surface active agents and the like in addition to the molecule of choice and may also include one or more active ingredients such as antimicrobial agents, anti-inflammatory agents, anesthetics, and the like. An adjuvant can also be a part of the carrier of the vaccine, in which case it can be selected by standard criteria based on the peptide used and the mode of administration and the subject (Arnon, R. (Ed.), 1987).

Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the peptides may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Effective dosages and schedules for administering a vaccine may be determined empirically, and making such determinations is within the skill in the art. The dosage ranges for the administration of a vaccine are those large enough to produce the desired effect in which the symptoms disorder are effected or in which *Nocardia farcinica* infection is prevented. By "prevent" is meant to minimize the chance that a subject will develop a *Nocardia farcinica* infection. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician or veterinarian in the event of any counterindications. Dosage can vary, and can be administered in one or more dose administrations daily, for one or several days.

If desired, a nucleic acid molecule of the invention can incorporate a detectable moiety. As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. Examples include (i) enzymes which can catalyze color or light emitting (luminescence) reactions and (ii) fluorophores. The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable is preferably employed. The detectable moiety may be inherent to a molecular probe. Common fluorescent moieties include: fluorescein, cyanine dyes, coumarins, phycoerythrin, phycobiliproteins, dansyl chloride, Texas Red, and lanthanide complexes.

The disclosed nucleotide sequences can be used as probes. By "probe," is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes specific for a given nucleic acid (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the nucleic acid to which they hybridize. Probes may be detectably-labeled, either radioactively, or non-radioactively, by methods well-known to those skilled in the art.

A detectably labeled nucleic acid molecule, probe, primer or nucleic acid fragment as disclosed herein can be used in hybridization assays, such as Southern or northern blots, screening genomic or cDNA libraries, solution hybridization, ELISA, PCR-ELISA, and in situ hybridization to cell or tissue samples. Probes, primers, and oligonucleotides are also used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis and electrophoretic mobility shift assay (EMSA). The disclosed nucleic acids or proteins can be placed on a chip or a micro array.

Provided herein are methods of identifying a *Nocardia farcinica* infection in a subject. In one aspect a method of identifying a *Nocardia farcinica* infection in a subject, comprising contacting DNA from the subject with the primer comprising the nucleotide sequence of SEQ ID NO:1 is provided. Also provided is a method of identifying a *Nocardia farcinica* infection in a subject, comprising contacting DNA from the subject with the primer comprising the nucleotide sequence of SEQ ID NO:2. Further provided is a method of identifying a *Nocardia farcinica* infection in a subject, comprising contacting DNA from the subject with a primer comprising a nucleotide sequence selected from the group consisting of SEQ ID NOS:3-39. The contacted DNA can be isolated from a subject or it can be contacted in situ.

Provided herein is a method of identifying a *Nocardia farcinica* infection in a subject, comprising detecting the presence of a polynucleotide consisting of the nucleotide sequence represented by SEQ ID NO:40, the presence of SEQ ID NO:40 being associated with *Nocardia farcinica* infection. Also provided herein is the method of identifying a *Nocardia farcinica* infection in a subject, comprising detecting the presence of a polynucleotide consisting of the nucleotide sequence represented by SEQ ID NO:40, the presence of SEQ ID NO:40 being associated with *Nocardia farcinica* infection, wherein the detection is by amplification using a *Nocardia farcinica*-specific primer comprising the nucleotide sequence of SEQ ID NO:48.

Further provided is a method of identifying a *Nocardia farcinica* infection in a subject, comprising detecting the presence of a polynucleotide consisting of the nucleotide sequence represented by SEQ ID NO:41. For example, methods are provided wherein the detection is by amplification using a *Nocardia farcinica*-specific primer comprising the nucleotide sequence of SEQ ID NO:1, or wherein the detection is by amplification using a *Nocardia farcinica*-specific primer comprising the nucleotide sequence of SEQ ID NO:2. Further provided is a method of identifying *Nocardia farcinica* infection in a subject by amplifying DNA from the subject using a *Nocardia farcinica*-specific primer comprising a nucleotide sequence selected from the group consisting of SEQ ID NOS:1-39, and detecting the presence of an amplification product, the presence of an amplification being associated with the presence of infection.

The disclosed methods of identifying a *Nocardia farcinica* infection may utilize PCR technologies. The technology of PCR permits amplification and subsequent detection of minute quantities of a target nucleic acid. Details of PCR are well described in the art, including, for example, U.S. Pat. No. 4,683,195 to Mullis et al., U.S. Pat. No. 4,683,202 to Mullis and U.S. Pat. No. 4,965,188 to Mullis et al., which are hereby incorporated by reference for their teaching of PCR methods. Generally, oligonucleotide primers are annealed to the denatured strands of a target nucleic acid, and primer extension products are formed by the polymerization of deoxynucleoside triphosphates by a polymerase. A typical PCR method involves repetitive cycles of template nucleic acid denaturation, primer annealing and extension of the annealed primers by the action of a thermostable polymerase. The process results in exponential amplification of the target nucleic acid, and thus allows the detection of targets existing in very low concentrations in a sample. PCR is widely used in a variety of applications, including biotechnological research, clinical diagnostics and forensics.

In the disclosed methods, the provided *Nocardia farcinica* specific primers may be used as the primers in a PCR protocol. Primers are typically used in pairs. Thus, by way of non-limiting example, SEQ ID NO:1 and SEQ ID NO:2 could be used together to amplify a region of *Nocardia farcinica* specific DNA using a PCR protocol. Such amplification would indicate the presence of, or infection by, *Nocardia farcinica*. Other disclosed primers could be combined into primer pairs and used to detect the presence of *Nocardia farcinica* infection in a subject. These combinations could detect the presence of SEQ ID NO:40, SEQ ID NO:41, or other *Nocardia farcinica* specific sequences internal to SEQ ID NO:40 or SEQ ID NO:41. The determination of effective combinations, given the disclosed primers represented by SEQ ID NOS:1-39, is routine to one skilled in the art. Appropriate primer pair combinations include any primer pair capable amplifying the disclosed *Nocardia farcinica* specific sequences or any fragment of these sequences. Examples of primer pairs are shown in example two. All appropriate combinations are hereby disclosed and provided.

In one aspect, the PCR assay is performed under high stringency conditions. High stringency conditions means conditions that allow specific amplification of *Nocardia farcinica* DNA. For example, high stringency PCR conditions could include a PCR cycle comprising 60 seconds at 94° C., 60 seconds at 55° C. and 60 seconds at 72° C. Other high stringency PCR conditions that would allow only specific amplification of *Nocardia farcinica* DNA could be readily determined by one skilled in the art. Such additional reaction conditions are disclosed herein.

As will be appreciated, numerous variations may be made to optimize the PCR amplification for any particular reaction. Other suitable target amplification methods include the ligase chain reaction (LCR; e.g., Wu, D. Y. and Wallace, R. B., Genomics 4 (1989) 560-9; Landegren, U., et al., Science 241 (1988) 1077-80; Barany, F., Proc Natl Acad Sci USA 88 (1991) 189-93; and Barringer, K. J., et al., Gene 89 (1990) 117-22); strand displacement amplification (SDA; e.g., Walker, G. T., et al., Proc Natl Acad Sci USA 89 (1992) 392-6); transcription amplification (e.g., Kwoh, D. Y., et al., Proc Natl Acad Sci USA 86 (1989) 1173-7); self-sustained sequence replication (3SR; e.g., Fahy, E., et al., PCR Methods Appl 1 (1991) 25-33; Guatelli, J. C., et al., Proc Natl Acad Sci USA 87 (1990) 1874-8); the nucleic acid sequence based amplification (NASBA, Cangene, Mississauga, Ontario; e.g., Compton, J., Nature 350 (1991) 91-2); the transcription-based amplification System (TAS); and the self-sustained sequence replication System (SSR).

One useful variant of PCR is PCR ELISA (e.g., Boehringer Mannheim Cat. No. 1636 111) in which digoxigenin-dUTP is incorporated into the PCR product. The PCR reaction mixture is denatured and hybridized with a biotin-labeled oligonucleotide designed to anneal to an internal sequence of the PCR product. The hybridization products are immobilized on streptavidin coated plates and detected using anti-digoxigenin antibodies. Examples of techniques sufficient to direct persons of skill through in vitro amplification methods are found in PCR Technology: Principles and Applications for DNA Amplification (1992), Eds. H. Erlich, Freemann Press, New York; PCR protocols: A guide to Methods and Applications (1990), Eds. Innis, Gelfand, Snisky and White, Academic Press, San Diego. By non limiting example, PCR ELISA has been described as a method for the identification of *Campylobacter jejuni* and *Camplobacter coli* (Sails et al., (2001) Mol. Cellular Probes 15:291-300, which is incorporated herein by reference for the methods taught therein), *Leishmania infantum* (Martin-Sanchez et al., (2001) Parisitology 122(6):607-15, which is incorporated herein by reference for the methods taught therein), *Listeria monocytogenes* (Scheu et al., (1999) Lett Appl Microbiol 29(6):416-20, which is incorporated herein by reference for the methods taught therein) and *Salmonella* (1999) Asian Pac J Allergy Immunol 17(1):41-51, which is incorporated herein by reference for the methods taught therein).

Amplified products may be directly analyzed, e.g., by size as determined by gel electrophoresis; by hybridization to a target nucleic acid immobilized on a solid support such as a bead, membrane, slide, or chip; by sequencing; immunologically, e.g., by PCR-ELISA, by detection of a fluorescent, phosphorescent, or radioactive signal; or by any of a variety of other well-known means. An illustrative example of a detection method uses PCR primers augmented with hairpin loops linked to fluorescein and a benzoic acid derivative that serves as a quencher, such that fluorescence is emitted only when the primers unfold to bind their targets and replication occurs.

In addition, methods known to increase the signal produced by amplification of the target sequence may be used. Methods for augmenting the ability to detect the amplified target include signal amplification system such as: branched DNA signal amplification (e.g., U.S. Pat. No. 5,124,246; Urdea, M. S., Biotechnology (N Y) 12 (1994) 926-8); tyramide signal amplification (TSA) System (DuPont); catalytic signal amplification (CSA; Dako); Q Beta Replicase Systems (Tyagi, S., et al., Proc Natl Acad Sci USA 93 (1996) 5395-400).

One of skill in the art will appreciate that whatever amplification method is used, a variety of quantitative methods known in the art can be used if quantitation is desired. Detailed protocols for quantitative PCR may be found in PCR protocols: A guide to Methods and Applications (1990), Eds. Innis, Gelfand, Snisky and White, Academic Press, San Diego and Ausubet et al., supra (Unit 15) and Diaco, R., Practical Considerations for the Design of Quantitative PCR Assays in "PCR STRATEGIES" (1995) 84-108, Eds. I. e. al., Academic Press, New York; U.S. Pat. No. 5,629,154.

Disclosed herein are kits that are drawn to reagents that can be used in practicing the methods disclosed herein. Provided herein is a kit for identifying *Nocardia farcinica* comprising a *Nocardia farcinica*-specific primer. An example of such a kit is a kit containing a primer comprising the nucleotide sequence of SEQ ID NO:1. Also provided is a kit comprising a *Nocardia farcinica*-specific primer comprising the nucleotide sequence of SEQ ID NO:2. Further provided is a kit comprising a *Nocardia farcinica*-specific primer comprising a nucleotide sequence selected from the group consisting of SEQ ID NOS:3-39. Also provided is a kit comprising a *Nocardia farcinica* specific primer comprising a nucleotide sequence capable of amplifying SEQ ID NO:41. The kits can include any reagent or combination of reagent discussed herein or that would be understood to be required or beneficial in the practice of the disclosed methods. For example, the kits could include primers to perform the amplification reactions discussed in certain aspects of the methods, as well as the buffers and enzymes required to use the primers as intended.

EXAMPLES

The following examples are put forth so as to provide those of ordinary skill in the art with a complete disclosure and description of how the compositions and/or methods claimed herein are made evaluated, and used, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for.

*Nocardia farcinica*-specific primers were designed for the rapid and specific identification of clinical and environmental isolates of *Nocardia farcinica* using a species-specific PCR assay. A simple and rapid PCR assay to rapidly and specifically identify *Nocardia farcinica* clinical isolates offers an alternative to the currently used physiologic methods and may allow earlier initiation of effective therapy, thus improving patient outcome. A PCR assay to identify *Nocardia farcinica* has significant advantages beyond both phenotypic and other molecular methods for the identification of clinical or environmental isolates. First, a significant reduction in time is required to make an identification. Once DNA was obtained the assay can be completed in 1 day in contrast to 1 week for commercially available biochemical identification (Biehle et al. (1996) J. Clin. Microbiol. 34: 103-107; Kiska et al., (2002) J. Clin. Microbiol. 40:1346-1351; Muir and Pritchard (1997) J. Clin. Microbiol. 35: 3240-3233) and 3 weeks for conventional biochemical identification (Berd (1973) Appl. Microbiol. 25: 665-681). Early identification is important for patient management. *Nocardia farcinica* has been shown to display a high degree of resistance to several antibiotics and requires prompt treatment with appropriate antimicrobial agents (Wallace et al., (1988) Antimicrob. Agents Chemother. 32:1776-1779; Wallace et al., (1990) J. Clin. Microbiol 28:2726-2732). Second, the RAPD-Ready-to-Go beads make PCR assays easier to prepare and more reproducible due to the reduction in pipeting errors and potential cross-contamination of reagents as well as helping to standardize reaction conditions. Third, the PCR assay using the Nf1/Nf2 primer set is performed at high stringency (55° C.) allowing only the specific amplification of *Nocardia farcinica* DNA. Other advantages include the requirement for relatively inexpensive equipment for analysis of template DNA. The PCR assay is easy to perform, the results are easy to interpret, and PCR is more sensitive than Southern blot methods. This PCR assay simplifies identification of this emerging bacterial pathogen and provides a useful tool in epidemiologic investigations and/or outbreaks (Manninen et al., (1993) Can. J. Microbiol. 39:635-641; Wenger et al., (1998) J. Infect. Dis. 178:1539-1543).

Example 1

Bacterial strains. A list of the type, reference, and clinical strains used in this study are shown in Table 1.

TABLE 1

| Microorganisms used in this study |
|---|
| *Deitzia maris* ATCC 35013$^T$ |
| *Gordonia aichiensis* ATCC 33611$^T$ |
| *Gordonia bronchialis* ATCC 25592$^T$ |
| *Gordonia rubropertincta* ATCC 14352$^T$ |
| *Gordonia sputi* ATCC 29627$^T$ |
| *Gordonia terrae* ATCC 25594$^T$ |
| *Gordonia/Rhodococcus* complex clinical isolates (Isik and Goodfellow (2002) Syst. Appl. Microbiol. 25: 60-67) |
| *Mycobacterium fortuitum* ATCC 6841$^T$ and 1 clinical isolate |
| *Mycobacterium peregrinum* ATCC 14467$^T$ and 1 clinical isolate |
| *Nocardia abscessus* clinical isolates (Blumel et al., (1998) J. Clin. Microbiol. 36: 118-122) |
| *Nocardia asteroides* ATCC 19247$^T$ |
| *Nocardia asteroides* sensu stricto clinical isolate (Berd (1973) Appl. Microbiol. 25: 665-681) |
| *Nocardia asteroides* sensu stricto type VI clinical isolates (Desmond and Flores (1993) FEMS Microbiol. Lett. 110: 281-284) |
| *Nocardia brasiliensis* ATCC 19296$^T$ and 6 clinical isolates |
| *Nocardia brevicatena* ATCC 15727, ATCC 15333, and 3 clinical isolates |
| *Nocardia farcinica* ATCC 3318$^T$ and 23 clinical isolates |
| *Nocardia nova* ATCC 33726$^T$, ATCC 33727, and 22 clinical isolates |
| *Nocardia otitidiscaviarum* ATCC 14629$^T$ and 4 clinical isolates |

TABLE 1-continued

| Microorganisms used in this study |
|---|
| *Nocardia transvalensis* ATCC 49872 and ATCC 49873 |
| *Rhodococcus coprophilus* ATCC 29080$^T$ |
| *Rhodococcus equi* ATCC 6939$^T$ and 4 clinical isolates |
| *Rhodococcus erythropolis* ATCC 4277$^T$ |
| *Rhodococcus fascians* ATCC 12974$^T$ |
| *Rhodococcus globerulus* ATCC 14898$^T$ |
| *Rhodococcus marinonascens* ATCC 35653$^T$ |
| *Rhodococcus opacus* ATCC 51882 |
| *Rhodococcus percolatus* ATCC 6348$^T$ |
| *Rhodococcus rhodnii* ATCC 35071$^T$ |
| *Rhodococcus rhodochrous* ATCC 13808$^T$ |
| *Rhodococcus wratislaviensis* ATCC 51786$^T$ |
| *Tsukamurella inchonensis* ATCC 700082$^T$ |
| *Tsukamurella paurometabola* ATCC 8368$^T$ |
| *Tsukamurella pulmonis* ATCC 700081$^T$ |
| *Tsukamurella tyrosinosolvens* DSM 44-234$^T$ |

ATCC, American Type Culture Collection (Manassas, Va.).
DSM, Deutsche Sammlung von Mikroorganismen Zellkulturen (Braunschweig, Germany).

Thirty-three type and reference strains were obtained from the American Type Culture Collection (ATCC), Manassas, Va. and the type strain *Tsukamurella tyrosinosolvens* DSM 44-234 was obtained from Deutsche Sammlung von Mikroorganismen Zellkulturen (DSM) (Braunschweig, Germany). The PCR assay primers were derived from the type strain, *Nocardia farcinica* ATCC 3318. The clinical and geographic sources and the patient's underlying conditions of the 26 clinical isolates of *Nocardia farcinica* are given in Table 2.

TABLE 2

*Nocardia farcinica* isolates used in this study

| Strain number | Clinical source | Geographic source | Underlying condition |
|---|---|---|---|
| W5185 | BAL | Georgia | Pneumonia |
| W5218 (ATCC 3318$^T$) | Foot wound | Not known | Mycetoma |
| W5492 | Sternal wound | Montana | Nosocomial infection |
| W5555 | Wound | Montana | Cancer |
| W5871 | BAL | France | AIDS |
| W5952 | Cutaneous | Montana | Not known |
| W6017 | Lung biopsy | Canada | Pneumonia |
| W6021 | Finger wound[a] | Georgia | Renal transplant |
| W6032 | Body fluid[a] | Georgia | Renal transplant |
| W6255 | Not given | New Jersey | Not known |
| W6434 (ATCC 23826) | Not given | Not known | Not known |
| W6500 | Post-operative infection | Ohio | Not known |
| W6544 | Eye | New Jersey | Not known |
| W6555 | Not given | India | Not known |
| W6859 | Not given | Minnesota | Not known |
| W6866 | Sputum | Canada | Pneumonia |
| W6889 | Chest wall | North Carolina | Cardiac surgery |
| W6925 | Lung biopsy | Delaware | Cancer |
| W6954 | Bronchial washing | Virginia | Not known |
| W6993 | Post-operative wound | Israel | CABG |
| W7015 | Foot wound | New York | Not known |

TABLE 2-continued

*Nocardia farcinica* isolates used in this study

| Strain number | Clinical source | Geographic source | Underlying condition |
|---|---|---|---|
| W7022 | Bronchial washing | Alabama | Not known |
| W7028 | Blood | Ohio | Acute abdomen |
| W7105 | Brain | Pennsylvania | Not known |
| W7119 | Sinus | Alabama | Not known |
| W7126 | Wound | South Carolina | Not known |
| W7130 | Bronchial washing | New York | Not known |
| W7131 | Blood | New York | Pulmonary fibrosis, diabetes, and malnutrition |

BAL, bronchial alveolar lavage;
CABG, coronary artery bypass graft.
[a]Isolates from the same patient with different ribotype patterns, The 66 *Nocardia* species and non-*Nocardia* isolates were obtained from the culture collection maintained by the Actinomycete Reference Laboratory, Meningitis and Special Pathogens Branch at the Centers for Disease Control and Prevention (Table 1). All isolates were identified by conventional physiologic and biochemical methods and susceptibility patterns, as previously described (Berd (1973) Appl. Microbiol. 25: 665-681; McNeil and Brown (2002) *Nocardia* pp. 481-500; Wallace et al., (1988) Antimicrob. Agents Chemother. 32:1776-1779; Wallace et al., (1990) J. Clin. Microbiol 28:2726-2732).

DNA preparation. Single colonies, were inoculated onto Lowenstein-Jensen slants (Remel, Lenexa, Kans.), checked for purity on heart infusion agar with 5% rabbit blood (BBL, Microbiology Systems, Cockeysville, Md.), and incubated at 35° C., generally for at least 16 h. The growth was harvested and suspended in 1.5 ml 10 mM Tris-1 mM EDTA (pH 8.0) and adjusted to a turbidity of a McFarland 4 standard. Then, 0.15 mm silica beads were added to 0.5 ml of the resultant stationary-phase culture. Samples were then submerged in boiling water bath for 15 min, followed by an immediate cell disruption in the Mini-beadbeater for 5 min. Bacterial lysates were clarified by three successive centrifugations at 15,000 rpm for 5 min. Template DNA was stored frozen at −20° C.

RAPD analysis of amplicons. Each RAPD reaction mixture contained 1 μl of template DNA, 2.0 μM primer, DKU49 (5'-CCGCCGACCGAG-3') (SEQ ID NO:48), one Ready-To-Go RAPD Analysis bead (Amersham Pharmacia Biotech, Piscataway, N.J.), and 21.5 μl distilled water. RAPD reaction conditions were previously described by Exmelin et al. (10, which is incorporated herein for its teaching of the RAPD method) except an Applied Biosystems (Foster City, Calif.) Gene Amp PCR System 9700 thermal cycler was used. Following amplification, a 15 μl sample was electrophoresed through a 2.5% agarose gel (1.5% of NuSieve [FMC Bioproducts, Rockland, Me.] and 1% of Agarose [Life Technologies, Grand Island, N.Y.]). Gels were stained with ethidium bromide (0.5 μg/ml), and then photographed. An intense 409-bp band was observed in the lane for *Nocardia farcinica* ATCC 3318$^T$. The 409-bp band was excised with a razor and DNA from the excised fragment was purified using the buffers and the protocol included in the Qiagen Gel Extraction Kit (Qiagen, Chatsworth, Calif.).

DNA sequencing. The purified 409-bp RAPD fragment (SEQ ID NO:40) was cloned into the multiple cloning site of plasmid pCR-2.1 and then used to transform *Escherichia coli* strain TOP10F using the reagents and protocols supplied by the manufacturer for the Original TA Cloning Kit (Invitrogen Corp., San Diego, Calif.). Plasmid DNA containing the RAPD fragment was purified by using the protocol and reagents supplied with the Plasmid Midi Protocol (Qiagen). Using primers M13 Reverse and T7 promoter (Invitrogen), both strands of the fragment were sequenced from three independent clones in their entirety using the ABI PRISM BigDye Terminator Cycle Sequencing Ready Reaction Kit (Perkin-Elmer, Applied Biosystems, Foster City, Calif.) with the manufacturer's reagents and recommendations for cycle sequencing. Centrisep columns (Princeton Separations, Adelphia, N.J.) were used to remove unincorporated dye-labeled and unlabeled nucleotides. Sequencing reactions were resolved and analyzed using an ABI PRISM 310 Genetic Analyzer (Applied Biosystems). Sequencher version 4.05 software (Gene Codes Corp., Ann Harbor, Mich.) was used to edit and align the sequence data.

*Nocardia farcinica*-specific PCR. Based on the nucleotide sequence of the 409-base-pair DNA fragment, species-specific PCR primer pairs, Nf1 (5'-CCGCAGACCACGCAAC) (SEQ ID NO:1) and Nf2 (5'-ACGAGGTGACGGCTGC) (SEQ ID NO:2) were designed using the OLIGO 4.0 program (National Biosciences, Plymouth, Minn.). A 314-bp fragment was expected following PCR amplification of *Nocardia farcinica* DNA with primer Nf1 and Nf2. PCR reactions consisted of 10 mM Tris-HCl, pH 8.3, 50 mM KCl, 1.5 mM $MgCl_2$, 0.2 μM of primers Nf1 and Nf2, and 1 to 5 μl of genomic DNA, 0.2 mM for each deoxynucleotide triphosphate (dATP, dCTP, dGTP, and dTTP), and 2.5 units of Taq DNA polymerase in a volume of 50 μl. PCR was performed in a Gene Amp PCR System 9700 thermal cycler. Each cycle was comprised of 60 s at 94° C., 60 s at 55° C., and 60 s at 72° C. Following amplification, a 15 μl sample was separated and electrophoresed on 1.5% agarose gels, stained with ethidium bromide (0.5 μg/ml), and then photographed. Following amplification, a 15 μl sample was separated by electrophoresis on 1.5% agarose gels, stained with ethidium bromide (0.5 μg/ml), and then photographed.

Specificity of PCR assays. Specificity of the PCR reactions was confirmed by two methods. Amplicons obtained following PCR with the primer pairs Nf1 and Nf2 were purified using reagents and methods supplied with the QIAquick PCR Purification Kit (Qiagen, Valencia, Calif.). Purified PCR amplicons were digested with restriction endonuclease (CfoI) (Roche Molecular Biochemicals, Indianapolis, Ind.) at 37° C. in the buffer recommended by the manufacturer and the digestion was resolved through a 2.5% NuSieve agarose gel. Two CfoI fragments of 218, and 78 bp were expected to be observed on ethidium bromide stained gels but not the 18 bp fragment located between CfoI sites. The specificity of the 314-bp fragment was also confirmed by direct sequencing in both directions of 100 ng of PCR amplified template using Nf1 and Nf2 as sequencing primers for *Nocardia farcinica* strains W6954, W6021, W6032, W6889, and ATCC $3318^T$ using the ABIPRISM BigDye Terminator Cycle Sequencing Ready Reaction Kit (Perkin-Elmer).

RESULTS

RAPD profiles.

RAPD profiles generated by using primer DKU49 were previously found to be useful for typing isolates of *Nocardia farcinica* obtained from a nosocomial outbreak in heart transplant recipients (Exmelin et al., J. Clin. Microbiol. 34: 1014-1016). Our initial comparison of RAPD profiles generated by primer DKU49 of *Nocardia farcinica* isolates, other *Nocardia* species, and related species of aerobic actinomycetes indicated its potential utility for identification of *Nocardia farcinica* isolates (Lentnek et al., $37^{th}$ ICAAC, abstr. D-75). Representative RAPD profiles of *N. nova, Nocardia farcinica, N. brasiliensis, N. transvalensis, N. asteroides, N. asteroides* sensu stricto drug patterns 1 (*N. abscessus*) and 6 (*N. cyriacigeorgica*), and *Mycobacterium fortuitum* generated with primer DKU49 are shown in FIG. 1. RAPD profiles for four isolates of *Nocardia farcinica* showed 9 to 14 bands ranging in size from 200 bp (FIG. 1, lane 7) to >2 kb (FIG. 1, lane 6). While several bands between strains were polymorphic, an intense fragment of approximately 409 bp for all four *Nocardia farcinica* isolates (FIG. 1, lanes 4-7) was observed. Although the 409-bp band appeared species-specific for *Nocardia farcinica*, bands approximately this size were observed also for closely related species such as M fortuitum (FIG. 1, lane 9) and *N. asteroides* (FIG. 1, lane 12). Therefore, the 409-bp fragment of *Nocardia farcinica* was excised from an agarose gel and purified.

Cloning and nucleotide sequence of the 409-bp RAPD fragment. To further characterize the 409-bp fragment amplified by DKU49 under low stringency conditions, the purified fragment was subcloned into pCR-2.1. Three independent subclones were sequenced in both directions. The DNA sequence of the subclones were identical suggesting the 409-bp fragment was composed of a single homologous DNA element. Whether the 409-bp fragment was unique to *Nocardia farcinica* or found in other species of bacteria was determined next. Using BLASTN the 409-bp sequence was found not to have any significant homology to any genes or sequences available in the GenBank data base.

PCR assay design and confirmation. Obtaining reproducible RAPD profiles and the changes in the intensities of observed bands hampers widespread use of this method for clinical identification. RAPD analysis requires adherence to rigorous reaction conditions. Variability of RAPD profiles due to annealing of short primers at low stringency conditions leads to mismatch hybridization to the non-perfectly complementary target sequences (Ellsworth et al., (1993) BioTechniques 14:214-217) and demonstrates the need for a more specific PCR-based test. To achieve a more specific and reproducible PCR-based assay for *Nocardia farcinica*, primers complementary to the 409-bp target sequence were designed. The nucleotide sequences for primers Nf1 and Nf2 are shown in FIG. 2 (SEQ ID NOS:1 and 2). Following amplification of purified *Nocardia farcinica* genomic DNA at 55° C., a PCR fragment of 314 bp is expected but not from DNA obtained from other bacterial species. FIG. 3 shows a typical agarose gel of the amplification products obtained for 16 *Nocardia farcinica* clinical isolates amplified using Nf1 and Nf2 primer set; a 314-bp band was observed for all 24 isolates of *Nocardia farcinica* examined (Table 2). To verify that amplification of *Nocardia farcinica* with the Nf1/Nf2 primer set amplifies only the expected 314-bp DNA sequence, the 314-bp fragment was digested with the restriction endonuclease CfoI, which contains two CfoI restriction endonuclease sites (FIG. 2) After digestion, three restriction endonuclease fragments of 218, 78 and 18 bp are expected (See SEQ ID NOS:42, 44, 43). A typical pattern of CfoI restriction fragments is shown in FIG. 4 and, except that the 18-bp fragment was not visualized, corresponds to the predicted molecular sizes demonstrating suggesting the specific amplification of *Nocardia farcinica* 314-bp DNA fragment.

To further elucidate the specificity of the PCR product using the Nf1/Nf2 primer set, the nucleotide sequence for the 314-bp product obtained from five different isolates of *Nocardia farcinica* was determined. The DNA nucleotide sequences of the 314-bp DNA fragment was identical for all five strains and identical to the appropriate region of the 409-bp RAPD fragment. The nucleotide sequence of the 314-bp fragment is shown in FIG. 2 (SEQ ID NO:41). BLAST searches identified no significant homology of the 314-bp fragment to any sequence deposited in the GenBank database. Analysis of the 314-bp fragment by CfoI digestion and nucleotide sequence analysis demonstrated suggests specific amplification of the *Nocardia farcinica* target sequence.

Specificity of the PCR assay. To determine the specificity of the PCR assay using the Nf1/Nf2 primer set, genomic DNAs from a total of 56 nocardial species isolates and 41 other bacterial species isolates phylogeneticaly related to the genus *Nocardia* were tested. The isolates analyzed are listed in Table 1. Whereas a 314-bp band was observed for all 24 isolates of *Nocardia farcinica*, no amplification products were observed for the other bacterial species suggesting the PCR assay is specific for *Nocardia farcinica* DNA.

Example 2

Disclosed are 122 primer pairs capable of amplifying portions of SEQ ID NO:40 and 41. These 122 primer pairs are intended to be purely exemplary and are not intended to limit the scope of what the inventors regard as their invention. One of skill in the art could readily identify additional primer pairs that would amplify portions of SEQ ID NO:40 and 41, and these additional primers are considered to be disclosed herein.

Each primer pair is numbered 1-122 in the list below. The nucleotide sequence of the forward primer is shown first, followed by the reverse member of the primer pair. Following the reverse primer pair is a set of five numbers, each on a different line of text. The first number is a quality score, the second number is the expected length of the PCR product using the primer pair, the third number is the calculated difference in Tm (between 0 to 5 C), the fourth number is the position of the forward primer relative to nucleotide 1 of SEQ ID NO:40, and the fifth number is the position of the reverse primer relative to nucleotide 1 of SEQ ID NO:40.

```
1
 CAACAACGCCGCCTCGA (SEQ ID NO:3)
        AGGCTGCGGTGGATGTCA (SEQ ID NO:31)
               810
                 352
                    0
                      28
                     380

2
 AACGCCGCCTCGATCTCA (SEQ ID NO:4)
        AGGCTGCGGTGGATGTCA (SEQ ID NO:31)
```

-continued

```
               808
                 348
                    0
                      32
                     380

3
 CGCCTCGATCTCACCCAA (SEQ ID NO:5)
        AGGCTGCGGTGGATGTCA (SEQ ID NO:31)
               806
                 343
                    1
                      37
                     380

4
 CGATCTCACCCAACTCGA (SEQ ID NO:6)
        AGGCTGCGGTGGATGTCA (SEQ ID NO:31)
               803
                 338
                    4
                      42
                     380

5
 CCCAACTCGATCCGCAGA (SEQ ID NO:7)
        AGGCTGCGGTGGATGTCA (SEQ ID NO:31)
               801
                 330
                    1
                      50
                     380

6
 AACTCGATCCGCAGACCA (SEQ ID NO:8)
        AGGCTGCGGTGGATGTCA (SEQ ID NO:31)
               799
                 327
                    2
                      53
                     380

7
 GATCCGCAGACCACGCAA (SEQ ID NO:9)
        AGGCTGCGGTGGATGTCA (SEQ ID NO:31)
               798
                 322
                    0
                      58
                     380

8
 CACGCAACTTCACCTGGA (SEQ ID NO:10)
        AGGCTGCGGTGGATGTCA (SEQ ID NO:31)
               793
                 311
                    3
                      69
                     380

9
 ACGCAACTTCACCTGGAA (SEQ ID NO:11)
        AGGCTGCGGTGGATGTCA (SEQ ID NO:31)
               792
                 310
                    4
                      70
                     380

10
 GAAGTCCGTACGCCCCAA (SEQ ID NO:12)
        AGGCTGCGGTGGATGTCA (SEQ ID NO:31)
               787
                 295
                    1
                      85
                     380

11
 CAACAACGCCGCCTCGA (SEQ ID NO:3)
```

-continued

GGTCGTCCGGTGTGGAA (SEQ ID NO:32)
785
291
1
28
319

12
AACGCCGCCTCGATCTCA (SEQ ID NO:4)
GGTCGTCCGGTGTGGAA (SEQ ID NO:32)
783
287
2
32
319

13
CGCCTCGATCTCACCCAA (SEQ ID NO:5)
GGTCGTCCGGTGTGGAA (SEQ ID NO:32)
782
282
0
37
319

14
CGATCTCACCCAACTCGA (SEQ ID NO:6)
GGTCGTCCGGTGTGGAA (SEQ ID NO:32)
779
277
2
42
319

15
CAACAACGCCGCCTCGA (SEQ ID NO:3)
GCGGGTGTTCGTGTTGGA (SEQ ID NO:33)
778
270
0
28
298

16
AACGCCGCCTCGATCTCA (SEQ ID NO:4)
GCGGGTGTTCGTGTTGGA (SEQ ID NO:33)
777
266
0
32
298

17
CCCAACTCGATCCGCAGA (SEQ ID NO:7)
GGTCGTCCGGTGTGGAA (SEQ ID NO:32)
777
269
0
50
319

18
CTCACCGGACTTCGTCCA (SEQ ID NO:13)
AGGCTGCGGTGGATGTCA (SEQ ID NO:31)
777
268
2
112
380

19
AACTCGATCCGCAGACCA (SEQ ID NO:8)
GGTCGTCCGGTGTGGAA (SEQ ID NO:32)
775
266
0
53
319

20

-continued

CGCCTCGATCTCACCCAA (SEQ ID NO:5)
GCGGGTGTTCGTGTTGGA (SEQ ID NO:33)
775
261
1
37
298

21
ACTTCGTCCACGCCACCA (SEQ ID NO:14)
AGGCTGCGGTGGATGTCA (SEQ ID NO:31)
775
260
0
120
380

22
CAACAACGCCGCCTCGA (SEQ ID NO:3)
GTTGGATGCGCGGTTGCA (SEQ ID NO:34)
774
258
1
28
286

23
GATCCGCAGACCACGCAA (SEQ ID NO:9)
GGTCGTCCGGTGTGGAA (SEQ ID NO:32)
774
261
2
58
319

24
CTTCGTCCACGCCACCAA (SEQ ID NO:15)
AGGCTGCGGTGGATGTCA (SEQ ID NO:31)
774
259
0
121
380

25
CGATCTCACCCAACTCGA (SEQ ID NO:6)
GCGGGTGTTCGTGTTGGA (SEQ ID NO:33)
773
256
4
42
298

26
AACGCCGCCTCGATCTCA (SEQ ID NO:4)
GTTGGATGCGCGGTTGCA (SEQ ID NO:34)
773
254
0
32
286

27
CACGCCACCAAATCACCA (SEQ ID NO:16)
AGGCTGCGGTGGATGTCA (SEQ ID NO:31)
772
252
2
128
380

28
CGCCTCGATCTCACCCAA (SEQ ID NO:5)
GTTGGATGCGCGGTTGCA (SEQ ID NO:34)
771
249
2
37
286

-continued

```
29
  CCCAACTCGATCCGCAGA (SEQ ID NO:7)
         GCGGGTGTTCGTGTTGGA (SEQ ID NO:33)
                  771
                    248
                       1
                          50
                         298

30
  ACGCAACTTCACCTGGAA (SEQ ID NO:11)
         GGTCGTCCGGTGTGGAA (SEQ ID NO:32)
                  770
                    249
                       1
                          70
                         319

31
  CACGCAACTTCACCTGGA (SEQ ID NO:10)
         GGTCGTCCGGTGTGGAA (SEQ ID NO:32)
                  770
                    250
                       0
                          69
                         319

32
  CGATCTCACCCAACTCGA (SEQ ID NO:6)
         GTTGGATGCGCGGTTGCA (SEQ ID NO:34)
                  769
                    244
                       5
                          42
                         286

33
  AACTCGATCCGCAGACCA (SEQ ID NO:8)
         GCGGGTGTTCGTGTTGGA (SEQ ID NO:33)
                  769
                    245
                       2
                          53
                         298

34
  GATCCGCAGACCACGCAA (SEQ ID NO:9)
         GCGGGTGTTCGTGTTGGA (SEQ ID NO:33)
                  768
                    240
                       0
                          58
                         298

35
  CCCAACTCGATCCGCAGA (SEQ ID NO:7)
         GTTGGATGCGCGGTTGCA (SEQ ID NO:34)
                  767
                    236
                       2
                          50
                         286

36
  GTGCGATACAACCGCGAA (SEQ ID NO:17)
         AGGCTGCGGTGGATGTCA (SEQ ID NO:31)
                  766
                    234
                       2
                         146
                         380

37
  GAAGTCCGTACGCCCCAA (SEQ ID NO:12)
         GGTCGTCCGGTGTGGAA (SEQ ID NO:32)
                  766
                    234
                       1
                          85
                         319
```

-continued

```
38
  AACTCGATCCGCAGACCA (SEQ ID NO:8)
         GTTGGATGCGCGGTTGCA (SEQ ID NO:34)
                  765
                    233
                       3
                          53
                         286

39
  GATCCGCAGACCACGCAA (SEQ ID NO:9)
         GTTGGATGCGCGGTTGCA (SEQ ID NO:34)
                  765
                    228
                       1
                          58
                         286

40
  TACAACCGCGAACCCACA (SEQ ID NO:18)
         AGGCTGCGGTGGATGTCA (SEQ ID NO:31)
                  764
                    228
                       2
                         152
                         380

41
  CACGCAACTTCACCTGGA (SEQ ID NO:10)
         GCGGGTGTTCGTGTTGGA (SEQ ID NO:33)
                  764
                    229
                       2
                          69
                         298

42
  ACGCAACTTCACCTGGAA (SEQ ID NO:11)
         GCGGGTGTTCGTGTTGGA (SEQ ID NO:33)
                  764
                    228
                       3
                          70
                         298

43
  AACCGCGAACCCACACCA (SEQ ID NO:19)
         AGGCTGCGGTGGATGTCA (SEQ ID NO:31)
                  764
                    225
                       0
                         155
                         380

44
  CGAACCCACACCACCGAA (SEQ ID NO:20)
         AGGCTGCGGTGGATGTCA (SEQ ID NO:31)
                  762
                    220
                       1
                         160
                         380

45
  CACGCAACTTCACCTGGA (SEQ ID NO:10)
         GTTGGATGCGCGGTTGCA (SEQ ID NO:34)
                  761
                    217
                       4
                          69
                         286

46
  GAAGTCCGTACGCCCCAA (SEQ ID NO:12)
         GCGGGTGTTCGTGTTGGA (SEQ ID NO:33)
                  760
                    213
                       1
                          85
```

-continued

```
                298

47
  ACGCAACTTCACCTGGAA (SEQ ID NO:11)
         GTTGGATGCGCGGTTGCA (SEQ ID NO:34)
                760
                  216
                     5
                       70
                      286

48
  ACCGAACGGATTCGCACA (SEQ ID NO:21)
         AGGCTGCGGTGGATGTCA (SEQ ID NO:31)
                759
                  208
                     1
                      172
                      380

49
  CTCACCGGACTTCGTCCA (SEQ ID NO:13)
         GGTCGTCCGGTGTGGAA (SEQ ID NO:32)
                758
                  207
                     0
                      112
                      319

50
  GAAGTCCGTACGCCCCAA (SEQ ID NO:12)
         GTTGGATGCGCGGTTGCA (SEQ ID NO:34)
                757
                  201
                     2
                       85
                      286

51
  ACTTCGTCCACGCCACCA (SEQ ID NO:14)
         GGTCGTCCGGTGTGGAA (SEQ ID NO:32)
                756
                  199
                     2
                      120
                      319

52
  CTTCGTCCACGCCACCAA (SEQ ID NO:15)
         GGTCGTCCGGTGTGGAA (SEQ ID NO:32)
                755
                  198
                     1
                      121
                      319

53
  CAAACCGATCCGCCGTCA (SEQ ID NO:22)
         AGGCTGCGGTGGATGTCA (SEQ ID NO:31)
                755
                  192
                     0
                      188
                      380

54
  CAACAACGCCGCCTCGA (SEQ ID NO:3)
         TCAGCTGGCGTTGGGGTA (SEQ ID NO:35)
                755
                  195
                     0
                       28
                      223

55
  AACGCCGCCTCGATCTCA (SEQ ID NO:4)
         TCAGCTGGCGTTGGGGTA (SEQ ID NO:35)
                754
                  191
                     0
```

-continued

```
                       32
                      223

56
  CACGCCACCAAATCACCA (SEQ ID NO:16)
         GGTCGTCCGGTGTGGAA (SEQ ID NO:32)
                754
                  191
                     0
                      128
                      319

57
  CGCCTCGATCTCACCCAA (SEQ ID NO:5)
         TCAGCTGGCGTTGGGGTA (SEQ ID NO:35)
                753
                  186
                     1
                       37
                      223

58
  CAAATCCGGCCGACCCAA (SEQ ID NO:23)
         AGGCTGCGGTGGATGTCA (SEQ ID NO:31)
                751
                  176
                     0
                      204
                      380

59
  ACTTCGTCCACGCCACCA (SEQ ID NO:14)
         GCGGGTGTTCGTGTTGGA (SEQ ID NO:33)
                751
                  178
                     0
                      120
                      298

60
  CTTCGTCCACGCCACCAA (SEQ ID NO:15)
         GCGGGTGTTCGTGTTGGA (SEQ ID NO:33)
                751
                  177
                     0
                      121
                      298

61
  CGATCTCACCCAACTCGA (SEQ ID NO:6)
         TCAGCTGGCGTTGGGGTA (SEQ ID NO:35)
                751
                  181
                     4
                       42
                      223

62
  CCCAACTCGATCCGCAGA (SEQ ID NO:7)
         TCAGCTGGCGTTGGGGTA (SEQ ID NO:35)
                750
                  173
                     1
                       50
                      223

63
  CTCACCGGACTTCGTCCA (SEQ ID NO:13)
         GTTGGATGCGCGGTTGCA (SEQ ID NO:34)
                750
                  174
                     3
                      112
                      286

64
  GTGCGATACAACCGCGAA (SEQ ID NO:17)
         GGTCGTCCGGTGTGGAA (SEQ ID NO:32)
                749
                  173
```

-continued

```
                    0
                      146
                      319

65
  AACTCGATCCGCAGACCA (SEQ ID NO:8)
         TCAGCTGGCGTTGGGGTA (SEQ ID NO:35)
                749
                  170
                    2
                       53
                      223

66
  CACGCCACCAAATCACCA (SEQ ID NO:16)
         GCGGGTGTTCGTGTTGGA (SEQ ID NO:33)
                749
                  170
                    2
                      128
                      298

67
  CCGACCCAAATACCCCAA (SEQ ID NO:24)
         AGGCTGCGGTGGATGTCA (SEQ ID NO:31)
                748
                  167
                    4
                      213
                      380

68
  TACAACCGCGAACCCACA (SEQ ID NO:18)
         GGTCGTCCGGTGTGGAA (SEQ ID NO:32)
                748
                  167
                    0
                      152
                      319

69
  CTTCGTCCACGCCACCAA (SEQ ID NO:15)
         GTTGGATGCGCGGTTGCA (SEQ ID NO:34)
                748
                  165
                    1
                      121
                      286

70
  ACTTCGTCCACGCCACCA (SEQ ID NO:14)
         GTTGGATGCGCGGTTGCA (SEQ ID NO:34)
                748
                  166
                    0
                      120
                      286

71
  GATCCGCAGACCACGCAA (SEQ ID NO:9)
         TCAGCTGGCGTTGGGGTA (SEQ ID NO:35)
                748
                  165
                    0
                       58
                      223

72
  AACCGCGAACCCACACCA (SEQ ID NO:19)
         GGTCGTCCGGTGTGGAA (SEQ ID NO:32)
                747
                  164
                    3
                      155
                      319

73
  CACGCCACCAAATCACCA (SEQ ID NO:16)
         GTTGGATGCGCGGTTGCA (SEQ ID NO:34)
                747
```

-continued

```
                  158
                    3
                      128
                      286

74
  TACCCCAACGCCAGCTGA (SEQ ID NO:25)
         AGGCTGCGGTGGATGTCA (SEQ ID NO:31)
                746
                  157
                    0
                      223
                      380

75
  CGAACCCACACCACCGAA (SEQ ID NO:20)
         GGTCGTCCGGTGTGGAA (SEQ ID NO:32)
                746
                  159
                    1
                      160
                      319

76
  CAACAACGCCGCCTCGA (SEQ ID NO:3)
         CGGATCGGTTTGTGCGAA (SEQ ID NO:36)
                746
                  154
                    1
                       28
                      182

77
  AACGCCGCCTCGATCTCA (SEQ ID NO:4)
         CGGATCGGTTTGTGCGAA (SEQ ID NO:36)
                745
                  150
                    2
                       32
                      182

78
  CACGCAACTTCACCTGGA (SEQ ID NO:10)
         TCAGCTGGCGTTGGGGTA (SEQ ID NO:35)
                745
                  154
                    3
                       69
                      223

79
  GTGCGATACAACCGCGAA (SEQ ID NO:17)
         GCGGGTGTTCGTGTTGGA (SEQ ID NO:33)
                745
                  152
                    1
                      146
                      298

80
  ACGCAACTTCACCTGGAA (SEQ ID NO:11)
         TCAGCTGGCGTTGGGGTA (SEQ ID NO:35)
                745
                  153
                    4
                       70
                      223

81
  AACGCCAGCTGATCACCA (SEQ ID NO:26)
         AGGCTGCGGTGGATGTCA (SEQ ID NO:31)
                745
                  151
                    1
                      229
                      380

82
  TACAACCGCGAACCCACA (SEQ ID NO:18)
         GCGGGTGTTCGTGTTGGA (SEQ ID NO:33)
```

-continued

```
744
  146
     1
       152
       298

83
  CGCCTCGATCTCACCCAA (SEQ ID NO:5)
         CGGATCGGTTTGTGCGAA (SEQ ID NO:36)
           744
             145
                0
                  37
                 182

84
  ACCGAACGGATTCGCACA (SEQ ID NO:21)
         GGTCGTCCGGTGTGGAA (SEQ ID NO:32)
           744
             147
                1
                 172
                 319

85
  AACCGCGAACCCACACCA (SEQ ID NO:19)
         GCGGGTGTTCGTGTTGGA (SEQ ID NO:33)
           744
             143
                1
                 155
                 298

86
  CGAACCCACACCACCGAA (SEQ ID NO:20)
         GCGGGTGTTCGTGTTGGA (SEQ ID NO:33)
           743
             138
                0
                 160
                 298

87
  GAAGTCCGTACGCCCCAA (SEQ ID NO:12)
         TCAGCTGGCGTTGGGGTA (SEQ ID NO:35)
           743
             138
                1
                  85
                 223

88
  GTGCGATACAACCGCGAA (SEQ ID NO:17)
         GTTGGATGCGCGGTTGCA (SEQ ID NO:34)
           743
             140
                3
                 146
                 286

89
  AGCTGATCACCAGCCAGA (SEQ ID NO:27)
         AGGCTGCGGTGGATGTCA (SEQ ID NO:31)
           743
             145
                3
                 235
                 380

90
  CGATCTCACCCAACTCGA (SEQ ID NO:6)
         CGGATCGGTTTGTGCGAA (SEQ ID NO:36)
           742
             140
                2
                  42
                 182

91
  TACAACCGCGAACCCACA (SEQ ID NO:18)
```

-continued

```
         GTTGGATGCGCGGTTGCA (SEQ ID NO:34)
           742
             134
                3
                 152
                 286

92
  CCCAACTCGATCCGCAGA (SEQ ID NO:7)
         CGGATCGGTTTGTGCGAA (SEQ ID NO:36)
           742
             132
                0
                  50
                 182

93
  CAAACCGATCCGCCGTCA (SEQ ID NO:22)
         GGTCGTCCGGTGTGGAA (SEQ ID NO:32)
           741
             131
                2
                 188
                 319

94
  ACCGAACGGATTCGCACA (SEQ ID NO:21)
         GCGGGTGTTCGTGTTGGA (SEQ ID NO:33)
           741
             126
                1
                 172
                 298

95
  AACCGCGAACCCACACCA (SEQ ID NO:19)
         GTTGGATGCGCGGTTGCA (SEQ ID NO:34)
           741
             131
                0
                 155
                 286

96
  CGAACCCACACCACCGAA (SEQ ID NO:20)
         GTTGGATGCGCGGTTGCA (SEQ ID NO:34)
           740
             126
                2
                 160
                 286

97
  AACTCGATCCGCAGACCA (SEQ ID NO:8)
         CGGATCGGTTTGTGCGAA (SEQ ID NO:36)
           740
             129
                0
                  53
                 182

98
  GATCCGCAGACCACGCAA (SEQ ID NO:9)
         CGGATCGGTTTGTGCGAA (SEQ ID NO:36)
           740
             124
                1
                  58
                 182

99
  ACCGAACGGATTCGCACA (SEQ ID NO:21)
         GTTGGATGCGCGGTTGCA (SEQ ID NO:34)
           739
             114
                2
                 172
                 286

100
```

-continued

CAAACCGATCCGCCGTCA (SEQ ID NO:22)
GCGGGTGTTCGTGTTGGA (SEQ ID NO:33)
738
110
0
188
298

101
CACGCAACTTCACCTGGA (SEQ ID NO:10)
CGGATCGGTTTGTGCGAA (SEQ ID NO:36)
738
113
0
69
182

102
CTCACCGGACTTCGTCCA (SEQ ID NO:13)
TCAGCTGGCGTTGGGGTA (SEQ ID NO:35)
738
111
1
112
223

103
CAAATCCGGCCGACCCAA (SEQ ID NO:23)
GGTCGTCCGGTGTGGAA (SEQ ID NO:32)
738
115
2
204
319

104
ACGCAACTTCACCTGGAA (SEQ ID NO:11)
CGGATCGGTTTGTGCGAA (SEQ ID NO:36)
738
112
1
70
182

105
CTTCGTCCACGCCACCAA (SEQ ID NO:15)
TCAGCTGGCGTTGGGGTA (SEQ ID NO:35)
737
102
0
121
223

106
ACTTCGTCCACGCCACCA (SEQ ID NO:14)
TCAGCTGGCGTTGGGGTA (SEQ ID NO:35)
737
103
0
120
223

107
GAAGTCCGTACGCCCCAA (SEQ ID NO:12)
CGGATCGGTTTGTGCGAA (SEQ ID NO:36)
736
97
0
85
182

108
CAAACCGATCCGCCGTCA (SEQ ID NO:22)
GTTGGATGCGCGGTTGCA (SEQ ID NO:34)
736
98
1
188
286

-continued

109
GATGCAACCGCGCATCCA (SEQ ID NO:28)
AGGCTGCGGTGGATGTCA (SEQ ID NO:31)
736
96
0
284
380

110
CCGACCCAAATACCCCAA (SEQ ID NO:24)
GGTCGTCCGGTGTGGAA (SEQ ID NO:32)
736
106
1
213
319

111
CACGCCACCAAATCACCA (SEQ ID NO:16)
TCAGCTGGCGTTGGGGTA (SEQ ID NO:35)
736
95
2
128
223

112
CAAATCCGGCCGACCCAA (SEQ ID NO:23)
GCGGGTGTTCGTGTTGGA (SEQ ID NO:33)
736
94
0
204
298

113
ATGCAACCGCGCATCCAA (SEQ ID NO:29)
AGGCTGCGGTGGATGTCA (SEQ ID NO:31)
736
95
0
285
380

114
CAACAACGCCGCCTCGA (SEQ ID NO:3)
TTTGGTGGCGTGGACGAA (SEQ ID NO:37)
736
94
0
28
122

115
CAACAACGCCGCCTCGA (SEQ ID NO:3)
ATTTGGTGGCGTGGACGA (SEQ ID NO:38)
736
95
0
28
123

116
CAACAACGCCGCCTCGA (SEQ ID NO:3)
GTGATTTGGTGGCGTGGA (SEQ ID NO:39)
736
98
2
28
126

117
AACGCCGCCTCGATCTCA (SEQ ID NO:4)
GTGATTTGGTGGCGTGGA (SEQ ID NO:39)
735
94
3
32
126

-continued

```
118
   AACGCCGCCTCGATCTCA (SEQ ID NO:4)
          ATTTGGTGGCGTGGACGA (SEQ ID NO:38)
                    735
                       91
                           1
                               32
                              123

119
   AACGCCGCCTCGATCTCA (SEQ ID NO:4)
          TTTGGTGGCGTGGACGAA (SEQ ID NO:37)
                    735
                       90
                           1
                               32
                              122

120
   AACGCCAGCTGATCACCA (SEQ ID NO:26)
          GGTCGTCCGGTGTGGAA (SEQ ID NO:32)
                    735
                       90
                           0
                              229
                              319

121
   TACCCCAACGCCAGCTGA (SEQ ID NO:25)
          GGTCGTCCGGTGTGGAA (SEQ ID NO:32)
                    735
                       96
                           2
                              223
                              319
```

-continued

```
122
   ACCGCGCATCCAACACGA (SEQ ID NO:30)
          AGGCTGCGGTGGATGTCA (SEQ ID NO:31)
                    735
                       90
                           1
                              290
                              380
```

In addition to the above 122 primer pairs, another primer pair, by way of non limiting example, is SEQ ID NO:1 and SEQ ID NO:2.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

Although the present process has been described with reference to specific details of certain embodiments thereof, it is not intended that such details should be regarded as limitations upon the scope of the invention except as and to the extent that they are included in the accompanying claims.

What is claimed is:

1. A method of identifying a *Nocardia farcinica* infection in a subject, comprising contacting DNA from the subject with a primer comprising the sequence of SEQ ID NO:1 and with a primer comprising the sequence of SEQ ID NO:2, and extending the primer comprising the sequence of SEQ ID NO:1 and the primer comprising the sequence of SEQ ID NO:2 to amplify at least a portion of the contacted DNA and detecting the amplified DNA to identify the *Nocardia farcinica* infection.

2. A kit for identifying *Nocardia farcinica* comprising a primer comprising the sequence of SEQ ID NO:1 and a primer comprising the sequence of SEQ ID NO:2.

3. A primer pair comprising a first primer comprising the nucleotide sequence of SEQ ID NO:1 and second primer comprising the nucleotide sequence of SEQ ID NO:2.

* * * * *

UNITED STATES PATENT AND TRADEMARK OFFICE

CERTIFICATE OF CORRECTION

PATENT NO. : 7,320,881 B2
APPLICATION NO. : 11/100338
DATED : January 22, 2008
INVENTOR(S) : Lasker et al.

It is certified that error appears in the above-identified patent and that said Letters Patent is hereby corrected as shown below:

On the Cover, Section 56, OTHER PUBLICATIONS:

Title page, Column 1, in Coyne *et al.* "from thw world" should read --from the world--.

Title page, Column 2, in Boiron *et al.* "*Nocardia,* nocardoisis and" should read --*Nocardia*, nocardiosis and--.

Second page, Column 1, in Lungu *et al.* "Differntiation of *Nocardia*" should read --Differentiation of *Nocardia*--.

Column 2, line 22, "J. Clin. Microbiol. 37: 99-102);" should read --J. Clin. Microbiol. 37: 99-102;--.

Column 3, line 15, "ATCC 6841 T;" should read --ATCC $6841^T$--.

Column 7, lines 31-32, "Cfo I" should read --CfoI--.

Column 7, line 32, "Cfo I" should read --CfoI--.

Column 7, lines 37-38, "Cfo I" should read --CfoI--.

Column 7, line 38 "Cfo I" should read --CfoI--.

Column 8, line 5, "of can be" should read --can be--.

Column 8, line 24, "of a putative" should read --of putative--.

Column 9, line 58, "symptoms disorder are effected" should read --symptoms or disorder are affected--.

Column 10, line 49, "northern" should read --Northern--.

Column 12, line 7, "capable amplifying" should read --capable of amplifying--.

Column 12, line 57, "*Camplobacter*" should read --*Campylobacter*--.

Column 13, line 16, "system" should read --systems--.

Column 13, line 29, "Ausubet" should read --Ausubel--.

Column 13, line 32, "Eds. I. e. al." should read --Eds. Innis. et. al.--.

Signed and Sealed this
Twenty-second Day of February, 2011

David J. Kappos
*Director of the United States Patent and Trademark Office*

Column 15, line 30, “patient’s” should read --patients’--.

Column 16, line 20, “patterns,” should read --patterns.--.

Column 17, line 22, “Harbor” should read --Arbor--.

Column 17, line 65, “ABIPRISM” should read --ABI PRISM--.

Column 18, line 27, “M fortuitum” should read --*M. fortuitum*--.

Column 19, line 2, “(Fig. 2)” should read --(Fig. 2).--.

Column 19, line 7, “demonstrating suggesting the” should read --suggesting the--.

Column 19, line 14, “was” should read --were--.

Column 19, line 27, “phylogeneticaly” should read --phylogentically--.

SEQUENCE LISTING

```
<160> NUMBER OF SEQ ID NOS: 54

<210> SEQ ID NO 1
<211> LENGTH: 16
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 1

ccgcagacca cgcaac                                                    16


<210> SEQ ID NO 2
<211> LENGTH: 16
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 2

acgaggtgac ggctgc                                                    16


<210> SEQ ID NO 3
<211> LENGTH: 17
<212> TYPE: DNA
<213> ORGANISM: Artificial Sequence
<220> FEATURE:
<223> OTHER INFORMATION: Description of Artifical Sequence; note =
```

-continued

```
      synthetic construct

<400> SEQUENCE: 3

caacaacgcc gcctcga                                                       17


<210> SEQ ID NO 4
<211> LENGTH: 18
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 4

aacgccgcct cgatctca                                                      18


<210> SEQ ID NO 5
<211> LENGTH: 18
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 5

cgcctcgatc tcacccaa                                                      18


<210> SEQ ID NO 6
<211> LENGTH: 18
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 6

cgatctcacc caactcga                                                      18


<210> SEQ ID NO 7
<211> LENGTH: 18
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 7

cccaactcga tccgcaga                                                      18


<210> SEQ ID NO 8
<211> LENGTH: 18
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 8

aactcgatcc gcagacca                                                      18


<210> SEQ ID NO 9
<211> LENGTH: 18
<212> TYPE: DNA
<213> ORGANISM: Artificial Sequence
<220> FEATURE:
<223> OTHER INFORMATION: Description of Artifical Sequence; note =
      synthetic construct
```

-continued

<400> SEQUENCE: 9
gatccgcaga ccacgcaa 18

<210> SEQ ID NO 10
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 10
cacgcaactt cacctgga 18

<210> SEQ ID NO 11
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 11
acgcaacttc acctggaa 18

<210> SEQ ID NO 12
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 12
gaagtccgta cgccccaa 18

<210> SEQ ID NO 13
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 13
ctcaccggac ttcgtcca 18

<210> SEQ ID NO 14
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 14
acttcgtcca cgccacca 18

<210> SEQ ID NO 15
<211> LENGTH: 18
<212> TYPE: DNA
<213> ORGANISM: Artificial Sequence
<220> FEATURE:
<223> OTHER INFORMATION: Description of Artifical Sequence; note =
synthetic construct -continued

<400> SEQUENCE: 15
cttcgtccac gccaccaa 18

<210> SEQ ID NO 16
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 16
cacgccacca aatcacca 18

<210> SEQ ID NO 17
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 17
gtgcgataca accgcgaa 18

<210> SEQ ID NO 18
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 18
tacaaccgcg aacccaca 18

<210> SEQ ID NO 19
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 19
aaccgcgaac ccacacca 18

<210> SEQ ID NO 20
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 20
cgaacccaca ccaccgaa 18

<210> SEQ ID NO 21
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 21

-continued accgaacgga ttcgcaca 18

<210> SEQ ID NO 22
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 22
caaaccgatc cgccgtca 18

<210> SEQ ID NO 23
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 23
caaatccggc cgacccaa 18

<210> SEQ ID NO 24
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 24
ccgacccaaa taccccaa 18

<210> SEQ ID NO 25
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 25
taccccaacg ccagctga 18

<210> SEQ ID NO 26
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 26
aacgccagct gatcacca 18

<210> SEQ ID NO 27
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 27

-continued agctgatcac cagccaga 18

<210> SEQ ID NO 28
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 28
gatgcaaccg cgcatcca 18

<210> SEQ ID NO 29
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 29
atgcaaccgc gcatccaa 18

<210> SEQ ID NO 30
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 30
accgcgcatc caacacga 18

<210> SEQ ID NO 31
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 31
aggctgcggt ggatgtca 18

<210> SEQ ID NO 32
<211> LENGTH: 17
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 32
ggtcgtccgg tgtggaa 17

<210> SEQ ID NO 33
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 33
gcgggtgttc gtgttgga 18

-continued

<210> SEQ ID NO 34
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 34
gttggatgcg cggttgca 18

<210> SEQ ID NO 35
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 35
tcagctggcg ttggggta 18

<210> SEQ ID NO 36
<211> LENGTH: 17
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 36
caacaacgcc gcctcga 17

<210> SEQ ID NO 37
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 37
tttggtggcg tggacgaa 18

<210> SEQ ID NO 38
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 38
atttggtggc gtggacga 18

<210> SEQ ID NO 39
<211> LENGTH: 18
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 39
gtgatttggt ggcgtgga 18

-continued

<210> SEQ ID NO 40
<211> LENGTH: 409
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 40
ccgccgaccg agcaacaccc ggctgcgcca acaacgccgc ctcgatctca cccaactcga 60
tccgcagacc acgcaacttc acctggaagt ccgtacgccc caaatactcc aactcaccgg 120
acttcgtcca cgccaccaaa tcaccggtgc gatacaaccg cgaacccaca ccaccgaacg 180
gattcgccac aaaccgatcc gccgtcaaat ccggccgacc caaatacccc aacgccagct 240
gatcaccagc cagatacaac tcacccgcaa cacccggcgc caccggatgc aaccgcgcat 300
ccaacacgaa cacccgcgtg ttccacaccg gacgaccgat cggcaccgac accacatccg 360
cagccgtcac ctcgtgataa gtgacatcca ccgcagcctc ggtcggcgg 409

<210> SEQ ID NO 41
<211> LENGTH: 314
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 41
ccgcagacca cgcaacttca cctggaagtc cgtacgcccc aaatactcca actcaccgga 60
cttcgtccac gccaccaaat caccggtgcg atacaaccgc gaacccacac caccgaacgg 120
attcgccaca aaccgatccg ccgtcaaatc cggccgaccc aaatacccca acgccagctg 180
atcaccagcc agatacaact cacccgcaac acccggcgcc accggatgca accgcgcatc 240
caacacgaac acccgcgtgt tccacaccgg acgaccgatc ggcaccgaca ccacatccgc 300
agccgtcacc tcgt 314

<210> SEQ ID NO 42
<211> LENGTH: 78
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 42
catccaacac gaacacccgc gtgttccaca ccggacgacc gatcggcacc gacaccacat 60
ccgcagccgt cacctcgt 78

<210> SEQ ID NO 43
<211> LENGTH: 18
<212> TYPE: DNA
<213> ORGANISM: Artificial Sequence
<220> FEATURE:
<223> OTHER INFORMATION: Description of Artifical Sequence; note =
      synthetic construct

<400> SEQUENCE: 43
ccaccggatg caaccgcg 18

<210> SEQ ID NO 44
<211> LENGTH: 78

-continued

<212> TYPE: DNA
<213> ORGANISM: Artificial Sequence
<220> FEATURE:
<223> OTHER INFORMATION: Description of Artifical Sequence; note =
synthetic construct

<400> SEQUENCE: 44
catccaacac gaacacccgc gtgttccaca ccggacgacc gatcggcacc gacaccacat 60
ccgcagccgt cacctcgt 78

<210> SEQ ID NO 45
<211> LENGTH: 252
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 45
ccaacaacgc cgcctcgatc tcacccaact cgatccgcag accacgcaac ttcacctgga 60
agtccgtacg ccccaaatac tccaactcac cggacttcgt ccacgccacc aaatcaccgg 120
tgcgatacaa ccgcgaaccc acaccaccga acggattcgc cacaaaccga tccgccgtca 180
aatccggccg acccaaatac cccaacgcca gctgatcacc agccagatac aactcacccg 240
caacacccgg cg 252

<210> SEQ ID NO 46
<211> LENGTH: 112
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 46
catccaacac gaacacccgc gtgttccaca ccggacgacc gatcggcacc gacaccacat 60
ccgcagccgt cacctcgtga taagtgacat ccaccgcagc ctcggtcggc gg 112

<210> SEQ ID NO 47
<211> LENGTH: 27
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 47
ccgccgaccg agcaacaccc ggctgcg 27

<210> SEQ ID NO 48
<211> LENGTH: 12
<212> TYPE: DNA
<213> ORGANISM: Artificial Sequence
<220> FEATURE:
<223> OTHER INFORMATION: Description of Artifical Sequence; note =
synthetic construct

<400> SEQUENCE: 48
ccgccgaccg ag 12

<210> SEQ ID NO 49
<211> LENGTH: 135
<212> TYPE: PRT
<213> ORGANISM: Artificial Sequence -continued

```
<220> FEATURE:
<223> OTHER INFORMATION: Description of Artifical Sequence; note =
      synthetic construct

<400> SEQUENCE: 49

Pro Pro Thr Glu Gln His Pro Ala Ala Pro Thr Thr Pro Pro Arg Ser
 1               5                  10                  15

His Pro Thr Arg Ser Ala Asp His Ala Thr Ser Pro Gly Ser Pro Tyr
            20                  25                  30

Ala Pro Asn Thr Pro Thr His Arg Thr Ser Ser Thr Pro Pro Asn His
        35                  40                  45

Gln Cys Asp Thr Thr Ala Asn Pro His His Arg Thr Asp Ser Pro Gln
    50                  55                  60

Thr Asp Pro Pro Ser Asn Pro Ala Asp Pro Asn Thr Pro Thr Pro Ala
65                  70                  75                  80

Asp His Gln Pro Asp Thr Thr His Pro Gln His Pro Ala Pro Pro Asp
                85                  90                  95

Ala Thr Ala His Pro Thr Arg Thr Pro Ala Cys Ser Thr Pro Asp Asp
            100                 105                 110

Arg Ser Ala Pro Thr Pro His Pro Gln Pro Ser Pro Arg Asp Lys His
        115                 120                 125

Pro Pro Gln Pro Arg Ser Ala
    130                 135


<210> SEQ ID NO 50
<211> LENGTH: 136
<212> TYPE: PRT
<213> ORGANISM: Artificial Sequence
<220> FEATURE:
<223> OTHER INFORMATION: Description of Artifical Sequence; note =
      synthetic construct

<400> SEQUENCE: 50

Arg Arg Pro Ser Asn Thr Arg Leu Arg Gln Gln Arg Arg Leu Asp Leu
 1               5                  10                  15

Thr Gln Leu Asp Pro Gln Thr Thr Gln Leu His Leu Glu Val Arg Thr
            20                  25                  30

Pro Gln Ile Leu Gln Leu Thr Gly Leu Arg Pro Arg His Gln Ile Thr
        35                  40                  45

Ser Ala Ile Gln Pro Arg Thr His Thr Thr Glu Arg Ile Arg His Lys
    50                  55                  60

Pro Ile Arg Arg Gln Ile Arg Pro Thr Gln Ile Pro Gln Arg Gln Leu
65                  70                  75                  80

Ile Thr Ser Gln Ile Gln Leu Thr Arg Asn Thr Arg Arg His Arg Met
                85                  90                  95

Gln Pro Arg Ile Gln His Glu His Pro Arg Val Pro His Arg Thr Thr
            100                 105                 110

Asp Arg His Arg His His Ile Arg Ser Arg His Leu Val Ile Ser Asp
        115                 120                 125

Ile His Arg Ser Leu Gly Arg Arg
    130                 135


<210> SEQ ID NO 51
<211> LENGTH: 132
<212> TYPE: PRT
<213> ORGANISM: Artificial Sequence
<220> FEATURE:
<223> OTHER INFORMATION: Description of Artifical Sequence; note =
      synthetic construct
```

-continued

<400> SEQUENCE: 51

```
Ala Asp Arg Ala Thr Pro Gly Cys Ala Asn Asn Ala Ala Ser Ile Ser
 1               5                  10                  15

Pro Asn Ser Ile Arg Arg Pro Arg Asn Phe Thr Trp Lys Ser Val Arg
            20                  25                  30

Pro Lys Tyr Ser Asn Ser Pro Asp Phe Val His Ala Thr Lys Ser Pro
        35                  40                  45

Val Arg Tyr Asn Arg Glu Pro Thr Pro Pro Asn Gly Phe Ala Thr Asn
    50                  55                  60

Arg Ser Ala Val Lys Ser Gly Arg Pro Lys Tyr Pro Asn Ala Ser Ser
65                  70                  75                  80

Pro Ala Arg Tyr Asn Ser Pro Ala Thr Pro Gly Ala Thr Gly Cys Asn
                85                  90                  95

Arg Ala Ser Asn Thr Asn Thr Arg Val Phe His Thr Gly Arg Pro Ile
            100                 105                 110

Gly Thr Asp Thr Thr Ser Ala Ala Val Thr Ser Val Thr Ser Thr Ala
        115                 120                 125

Ala Ser Val Gly
    130
```

<210> SEQ ID NO 52
<211> LENGTH: 21
<212> TYPE: DNA
<213> ORGANISM: Artificial Sequence
<220> FEATURE:
<223> OTHER INFORMATION: Description of Artifical Sequence; note = synthetic construct

<400> SEQUENCE: 52
ccaccgcagc ctcggtcggc g 21

<210> SEQ ID NO 53
<211> LENGTH: 20
<212> TYPE: DNA
<213> ORGANISM: Artificial Sequence
<220> FEATURE:
<223> OTHER INFORMATION: Description of Artifical Sequence; note = synthetic construct

<400> SEQUENCE: 53
gacccaaata ccccaacgcc 20

<210> SEQ ID NO 54
<211> LENGTH: 20
<212> TYPE: DNA
<213> ORGANISM: Artificial Sequence
<220> FEATURE:
<223> OTHER INFORMATION: Description of Artifical Sequence; note = synthetic construct

<400> SEQUENCE: 54
ccgatccgcc gtcaaatccg 20